US008951551B2

(12) United States Patent
Brown, Jr. et al.

(10) Patent No.: US 8,951,551 B2
(45) Date of Patent: Feb. 10, 2015

(54) MULTIRIBBON NANOCELLULOSE AS A MATRIX FOR WOUND HEALING

(75) Inventors: R. Malcolm Brown, Jr., Austin, TX (US); Wojciech Czaja, Austin, TX (US); Marc Jeschke, Galveston, TX (US); David J. Young, Elgin, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 367 days.

(21) Appl. No.: 11/513,564

(22) Filed: Aug. 31, 2006

(65) Prior Publication Data

US 2007/0053960 A1    Mar. 8, 2007

Related U.S. Application Data

(60) Provisional application No. 60/712,951, filed on Aug. 31, 2005.

(51) Int. Cl.
| | |
|---|---|
| *A61K 9/70* | (2006.01) |
| *A61K 38/18* | (2006.01) |
| *A61K 38/22* | (2006.01) |
| *A61L 15/16* | (2006.01) |
| *A61K 45/06* | (2006.01) |
| *A61K 31/56* | (2006.01) |
| *A61L 15/28* | (2006.01) |
| *A61L 27/20* | (2006.01) |
| *A61L 29/04* | (2006.01) |
| *A61L 31/04* | (2006.01) |
| *A61K 38/19* | (2006.01) |

(52) U.S. Cl.
CPC . *A61K 45/06* (2013.01); *A61K 9/70* (2013.01); *A61L 15/16* (2013.01); *A61K 9/7007* (2013.01); *A61K 31/56* (2013.01); *A61K 38/18* (2013.01); *A61L 15/28* (2013.01); *A61L 27/20* (2013.01); *A61L 29/043* (2013.01); *A61L 31/042* (2013.01); *A61K 38/191* (2013.01); *A61L 2400/12* (2013.01)
USPC ............. 424/445; 424/443; 424/447; 514/9.7

(58) Field of Classification Search
None
See application file for complete search history.

(56) References Cited

U.S. PATENT DOCUMENTS

| | | | | |
|---|---|---|---|---|
| 4,588,400 | A * | 5/1986 | Ring et al. | ................... 604/304 |
| 4,655,758 | A | 4/1987 | Ring et al. | |
| 4,912,049 | A | 3/1990 | Farah | |
| 5,081,158 | A | 1/1992 | Pomerantz | |
| 5,846,213 | A | 12/1998 | Wan | |
| 5,955,326 | A | 9/1999 | Bungay, III et al. | |
| 6,140,257 | A | 10/2000 | Kershaw et al. | |
| 6,258,586 | B1 | 7/2001 | Jussila | |
| 6,262,255 | B1 | 7/2001 | Mares-Guia | |
| 6,403,570 | B1 | 6/2002 | Soe et al. | |
| 6,458,460 | B1 | 10/2002 | Griffiths et al. | |
| 6,500,539 | B1 | 12/2002 | Chen et al. | |
| 6,500,777 | B1 | 12/2002 | Wiseman et al. | |
| 6,548,730 | B1 | 4/2003 | Patel et al. | |
| 6,800,753 | B2 | 10/2004 | Kumar | |
| 6,822,132 | B2 | 11/2004 | Ahrens et al. | |
| 6,906,036 | B2 | 6/2005 | Quirk et al. | |
| 2003/0088202 | A1 | 5/2003 | Gilman | |
| 2003/0225355 | A1 | 12/2003 | Butler | |
| 2004/0243043 | A1 | 12/2004 | McCarthy et al. | |
| 2005/0036955 | A1 | 2/2005 | DeGould | |
| 2005/0037082 | A1 | 2/2005 | Wan et al. | |

FOREIGN PATENT DOCUMENTS

| | | | | | |
|---|---|---|---|---|---|
| WO | WO 02/052028 | * | 7/2002 | .............. | C12P 19/04 |
| WO | 02/064817 | A1 | 8/2002 | | |
| WO | 02/064817 | A2 | 8/2002 | | |
| WO | WO 02/064817 | * | 8/2002 | .............. | C12Q 1/00 |
| WO | 2005/003366 | A1 | 1/2005 | | |
| WO | 2007/027849 | A2 | 3/2007 | | |

OTHER PUBLICATIONS

Meaning of "non-allergenic" available Dec. 6, 2003; accessed Feb. 19, 2009 at http://web.archive.org/web/20031206155442/http://www.allergybuyersclub.com/hypoallergenic.html.*
J D Fontana, et al. Acetobacter cellulose pellicle as a temporary skin substitute. Appl. Biochem. Biotechnol. (1990); 24(25); p. 253-264.*
Google translation of WO 02/052028.*
Pubmed Abstract of: Quinn, K. J., et al.; Biomaterials. 1985; 6(6); p. 369-377.*
Kondo, T. et al. PNAS (2002), 99(22); pp. 14008-14013.*
International Search Report and Written Opinion for PCT/US2006/033968 dated Aug. 10, 2007.
Rebello C, Almeida DA, Lima EM, Jr., Dornelas MP. Biofill um novo substituto de pele. Rev Bras Cir 1987; 77(6): 407-414.
Wouk AF, Diniz JM, Cirio SM, Santos H, Baltazar EL, Acco A. Membrana biologica (Biofill )—estudo comparativo com outros agentes promotores da cicatrizacao da pele em suinos: aspectos clinicos, histopatologicos e morfometricos. Arch Vet Scienc 1998; 3(1): 31-37 (abstract in English).
Balasubramani, et al., "Skin Substitutes: A Review," Burns, 2001; 27: 534-544.
Bielecki, et al., "Bacterial Cellulose," In: Steinbuchel A, editor. Biopolymers: Polysaccharides I. Wiley-VCH Verlag GmbH, Munster, Germany, 2002; 5:37-46.

(Continued)

*Primary Examiner* — Kevin S Orwig
(74) *Attorney, Agent, or Firm* — Edwin S. Flores; Daniel J. Chalker; Chalker Flores, LLP

(57) ABSTRACT

The present invention includes compositions and methods for the integration of a non-allergenic nanocellulose into a wound bed. The composition may be formed into a wide variety of implants, e.g., a suture, a sheet, a compress, a bandage, a band, a prosthesis, a fiber, a woven fiber, a bead, a strip, a clasp, a prosthesis, a catheter, a screw, a bone plate, a pin, a bandage or combinations thereof.

17 Claims, 13 Drawing Sheets

(56) References Cited

OTHER PUBLICATIONS

Brown, et al., "Cellulose Biosynthesis in *Acetobacter xylinum*: Visualization of the Site of Synthesis and Direct Measurement of the in vivo Process," Proc Nat Acad Sci USA, 1976; 73(12):4565-4569.
Czaja, et al., "Structural Investigations of Microbial Cellulose Produced in Stationary and Agitated Culture," Cellulose, 2004; 11:403-411.
Demling, et al., "Management of Partial Thickness Facial Burns (Comparison of Topical Antibiotics and Bioengineered Skin Substitutes)," Burns, 1999; 25: 256-261.
Evans, et al., "Palladium-Bacterial Cellulose Membranes for Fuel Cells," Biosensors and Bioelectronics, 2003; 18:917-923.
Gallin, et al., "Burn Healing in Organ Cultures of Embryonic Chicken Skin: A Model System," Burns, 1998; 24:613-620.
Innes, et al., "The Use of Silver Coated Dressings on Donor Site Wounds: A Prospective, Controlled Matched Pair Study," Burns, 2001; 27:621-627.
Jones, et al., "A Guide to Biological Skin Substitutes," British Journal of Plastic Surgery, 2002; 55:185-193.
Krystynowicz, et al., "The Evaluation of Usefulness of Microbial Cellulose as Wound Dressing Material," 14th Forum for Applied Biotechnology, Gent, Belgium, Proceedings Part I, Meded Fac Landbouwwet-Rijksuniv Gent, 2000, p. 213-220.
Krystynowicz, et al., "Factors Affecting the Yield and Properties of Bacterial Cellulose," Journal of Industrial Microbiology & Biotechnology, 2002; 29:189-195.
Latarjet, et al., "A Simple Guide to Burn Treatment," Burns, 1995; 21:221-225.
Martin, Paul, "Wound Healing-Aiming for Perfect Skin Regeneration," Science, 1997; 276:75-81.
Mayall, Rubens C., "Tratamento Das Ulceros Troficas Dos Membros Corn Um Novo Substitute Da Pele," Revista Brasileira de Cirurgia, 1990; 80(4):257-283 (abstract in English).
Nishi, et al., "The Structure and Mechanical Properties of Sheets Prepared from Bacterial Cellulose," Part 2: Improvement of the Mechanical Properties of Sheets and Their Applicability to Diaphragms of Electroacoustic Transducers, Journal of Materials Science, 1990; 25: 2997-3001.
Ross, et al., "Cellulose Biosynthesis and Function in Bacteria," Microbiol Rev, 1991; 55(1):35-58.
Shah, et al., "Towards Electronic Paper Displays Made from Microbial Cellulose," Appl Microbiol Biotechnol, 2005; 66 (4):352-355.
Vandamme, et al., "Improved Production of Bacterial Cellulose and its Application Potential," Polymer Degradation and Stability, 1998; 59:93-99.
Vloemans, et al., "A Newly Developed Hydrofibre Dressing, in the Treatment of Partial-Thickness Burns," Burns, 2001; 27:167-173.
Walker, et al., "Scanning Electron Microscopic Examination of Bacterial Immobilisation in a Carboxymethyl Cellulose (AQUACEL) and Alginate Dressings," Biomaterials, 2003; 24:883-890.
Watanabe, et al., "Structural Features and Properties of Bacterial Cellulose Produced in Agitated Culture," Cellulose, 1998; 5:187-200.
Winter, George D., "Formation of the Scab and the Rate of Epithelization of Superficial Wounds in the Skin of the Young Domestic Pig," Nature, 1962; 193:293-294.
U.S. Congress, Office of Technology Assessment, Biopolymers: Making Materials Nature's Way—Background Paper, OTA-BP-E-102 (Washington, DC: U.S. Government Printing Office, Sep. 1993): pp. 59-60.
Alvarez OM, Patel M, Booker J, Markowitz L. Effectiveness of a biocellulose wound dressing for the treatment of chronic venous leg ulcers: results of a single center randomized study involving 24 patients. Wounds 2004; 16 (7): 224-233.
Aung BJ. Diabetes watch: Does a new cellulose dressing have a potential in chronic wounds? Podiatry Today 2004; 17 (3): 20-26.
Brown RM, Jr. Microbial cellulose: A new resource for wood, paper, textiles, food and specialty products. Position Paper. 1999; Internet: http://www.botany.utexas.edu/facstaff/facpages/mbrown/position1.htm.
Czaja W, Kawecki M, Krystynowicz A, Wysota K, Sakiel S, Wroblewski P, Glik J, Bielecki S. Application of bacterial cellulose in treatment of second and third degree burns. The 227th ACS National Meeting, Anaheim, CA, USA, Mar. 28-Apr. 1, 2004.
Fontana JD, de Sousa AM, Fontana CK, Torriani IL, Moreschi JC, Gallotti BJ, de Sousa SJ, Narcisco GP, Bichara JA, Farah LF. Acetobacter cellulose pellicle as a temporary skin substitute. Applied biochemistry and biotechnology 1990; 4/25: 253-264.
Jonas R, Farah LH. Production and application of microbial cellulose. Polymer Degradation and Stability 1998; 59: 101-106.
Kucharzewski M, Slezak A, Franek A. Topical treatment of non-healing venous ulcers by cellulose membrane. Phlebologie 2003; 32: 147-51.
Quinn KJ, Courtney JM, Evans JH, Gaylor JDS, Reid WH. Principles of burn dressings. Biomaterials 1985; 6: 369-377.

\* cited by examiner

MULTIRIBBON NANOCELLULOSE AS A MATRIX FOR WOUND HEALING

TECHNICAL FIELD OF THE INVENTION

The present invention relates in general to the field of wound healing, and more particularly, to the use of a microbial cellulose nanomatrix for use as a wound dressing.

BACKGROUND OF THE INVENTION

This application claims priority to U.S. Provisional Patent Application Ser. No. 60/712,951, filed Aug. 31, 2005, the entire content of which is incorporated herein by reference. Without limiting the scope of the invention, its background is described in connection with artificial wound healing systems.

For example, in U.S. Pat. No. 6,906,036, issued to Quirk, et al., anti-aging and wound healing compounds are disclosed. These compounds include inhibitors of matrix metalloproteinases that are useful for encouraging the development of healthy skin and for treating wounds. The inhibitors are said to be peptides having sequences related to cleavage regions of the proenzyme forms of matrix metalloproteinases. The peptides were formulated into therapeutic compositions, lotions, creams, skin covering and wound dressings that facilitate healing and healthy skin development, discourage scarring and wrinkling and ameliorate the effects of healing.

Yet another example of a wound dressing is taught in U.S. Pat. No. 6,822,132, issued to Ahrens, et al. The dressing is said to be especially useful for covering wounds or preventing or treating blisters, in which a water vapor pervious carrier film uniformly covered with an adhesive layer, wherein there is centrally disposed on the adhesive layer a water vapor pervious polyurethane matrix that is beveled from an especially central point to the edge of the adhesive layer, although the periphery of the adhesive layer is at least partially not covered by the polyurethane matrix.

U.S. Pat. No. 6,140,257 teaches the use of composite fibers for wound dressings and a method for making same. An absorbent, composite fiber with a matrix of from 10% to less than 50% of water insoluble alginate having dispersed therein at least 40% of another polysaccharide is taught. Absorbent fibers for use in wound treatment are well known in the art, e.g., cellulose fibers, chemically modified cellulose fibers, pectin fibers, alginate fibers, chitosan fibers, hyaluronic acid fibers or other polysaccharide fibers or fibers derived from gums. In the treatment of wounds it is desirable to use fibers made from pectin or carboxymethyl cellulose but the known processes for making such fibers are complex and expensive and the resulting fibers not always viable. For instance it is known to make carboxymethyl cellulose fibers by chemically converting preformed cellulose fibers. It is also known that both pectin fibers and carboxymethyl cellulose fibers are difficult to spin.

SUMMARY OF THE INVENTION

The present invention is based on novel methods and compositions for the manufacture and use of a natural biopolymer, nanocellulose, for use in a novel wound healing system, and more particularly as a wound dressing for a wide variety of wound types, locations, shapes, depth and stage(s) of healing. One distinct advantage of the nanocellulose of the present invention is that is has been found to be non-allergenic, easy and inexpensive to manufacture and promotes natural host cellular migration to a wound site. Furthermore, nanocellulose is very moldable or has great conformability, which other materials available today lack. It has also been found that the present invention has a much finer nanostructure that is responsible for inducing wound healing, cell growth and consequently skin production.

The present invention will find particular application at donor sites (sites that the physician uses for harvesting skin for grafting in burns), partial thickness wounds (e.g., second degree burns, surgical wounds or wounds which still have the most of the dermis intact which can regenerate from the wound site). The nanocellulose of the present invention may be used in the treatment of burns, particularly intervention at the earliest possible time after the actual injury. The present invention may be provided in sterile form by emergency medical personnel having our materials on hand as an immediate temporary cover for all types of burn injuries, including physical wounding such as gunshots, knife cuts, bruises, contusions, lacerations, etc. Furthermore, the non-allergenic nature of the nanocellulose and its strength has the ability to rapidly stop the bleeding of wounds (haemostasis). The non-woven nanocellulose can also prevent the translocation of bacteria through it.

The present invention includes wound dressing that are made from a non-allergenic, nanocellulose substrate that has a strength that is greater than two time that of regular microbial cellulose. It has been found that certain types of nanocellulose are particularly well-suited for the treatment of different types of wounds. One particular problem with regular microbial cellulose of the prior art is that it is too expensive to manufacture, the bacterial strains loose their ability to synthesize cellulose are they are grown in culture and they fail to maintain their integrity during application. Furthermore, the methods of manufacture, processing and use of the regular microbial cellulose fails to provide a wound dressing that is suitable for use in a variety of wounds. While those regular microbial celluloses have found use in the laboratory, they have failed to satisfy users in the field.

One particular type of wound dressing of the present invention is a substrate that include a multi-ribbon cellulose produced by, e.g., *Acetobacter xylinum* (also known as Gluconoacetobacter). One a multi-ribbon cellulose of the present invention may be produced by *Acetobacter xylinum* strain NQ-5 under conditions in which the cellulose ribbons are deposited at the liquid gas interface and/or under shaking conditions. The wound dressing may be carboxymethyl-nanocellulose, a methyl-nanocellulose, a hydroxyethyl-nanocellulose, a hydroxypropyl-nanocellulose, a hydroxypropylmethyl-nanocellulose, mixtures or combinations thereof. The wound dressing may further include one or more active substances comprising a biologically active peptide, protein, agent, small molecule, substrate, lipid, carbohydrate, or combinations thereof. Some examples for biologically active molecules include, e.g., hyaluronan, β-1,3 glucan, carboxymethylcellulose, chitosan, a peptide, a growth factor, a hormone and mixtures and combinations thereof. The active substance may even be, e.g., steroid, anti-inflammatory, an antibiotic, a narcotic, a non-steroidal anti-inflammatory agent, an acetaminophen and combinations or mixtures thereof. Examples of biologically active proteins include, e.g., Derived Growth Factor, Becapiermin, Epidermal Growth Factor, Platelet Derived Endothelial Cell Growth Factor, Acidic Fibroblast Growth Factor, Basic Fibroblast Growth Factor, Transforming Growth Factor alpha, Transforming Growth Factor beta, Keratinocyte Growth Factor, Insulin-Like Growth Factor 1 or 2, Tumor Necrosis Factor and combinations or mixtures thereof.

When used in conjunction with a backing or other material that protects the wound dressing itself, the backing may be in the form of a layer or more cellulose (e.g., microbial or plant-based) based on a polyester, a polyurethane, a cellulose, a polyethylene glycol or derivative thereof, a vinyl pyrrolidone acrylic, a methacrylic acid, a silicone isobutylene, a isoprene or a styrene. The wound dressing may include a surface that is intended for application around a wound site and possesses adhesive properties.

The present invention also include compositions and methods for treating a skin wound, by, at least temporarily, implanting to the wound a sterile dressing comprising a non-allergenic, multi-ribbon nanocellulose. The skin wound may be a third degree wound. The wound dressing may include one or more active substances selected from agents that promote would healing, e.g., hyaluronan, β-1,3 glucan, carboxymethylcellulose, chitosan, various peptides, growth factors, hormones and combinations and mixtures thereof. Yet another embodiment of a method for treating a first, second or third degree wound, by attaching to a generally skin-less wound a sterile dressing comprising a non-allergenic, multi-ribbon nanocellulose and at least one active substance disposed in, on or about the multi-ribbon cellulose, wherein the active agent is disposed within the multi-ribbon nancelluose before, during or after the manufacture of the multi-ribbon nanocellulose.

Another method of the present invention includes treating a wound by permanently implanting a non-immunogenic, biodegradable nanocellulose substrate into a wound base, wherein the implanted substrate becomes at least partially integrated into the wound site. The substrate may become permanently integrated into the wound site. The multi-ribbon, nanocellulose substrate may be made by one or more prokaryotic organisms capable of generating cellulose selected from *Salmonella, Agrobacterium, Rhizobium*, any cyanobacterium that produces cellulose such as *Nostoc, Scytonema* or *Anabaena, Acetobacter* sp. and even *Acetobacter* multiribbon strain NQ 5. For example, the substrate may be an engineered nanostructure made-from dissolved and reprecipated celluloses including Nematic Ordered Cellulose.

Another method of the present invention includes the treatment of wounds without an immunogenic response by implanting a nanocellulose, e.g., multi-ribbon nanocellulose, dressing to a wound bed, wherein at least part of the dressing becomes permanently implanted and the multi-ribbon nanocellulose is manufacture to fit the wound site. Examples of methods for the specific manufacture of the wound site include the scanning of the target surface for the determination of width, length, depth and other surface characteristics at the wound site (e.g., crevices, bones, arteries/veins, curvature, texture). The method of manufacturing of the wound dressing may also include the step of growing at least one layer of a bacterial nanocellulose substrate in a vessel that serves as a template for the shape of the dressing, which template may be preformed based on, e.g., a scanned image or other measurements of the wound location. In fact, one or more wound dressings may be prefabricated to serve are replacements for the prior dressing during the recovery of the wound site, e.g., grafting operations in which the wound may take, days, weeks or even months to heal and/or for patients that have slow wound healing processes. For example, the nanocellulose may be grown, assembled or synthesized on a substrate that provides a template for the shape of the dressing, and the dressing comprises reservoirs for the external addition of one or more active agents or grown on a substrate that provides a template for the shape of the dressing, and the dressing comprises grooves for the growth of keratinocytes.

The nanocellulose may be regenerated in situ from regular cellulose ribbons into multi-ribbon cellulose. The regenerated cellulose may include one or more nanostructural features that promote stem cell, fibroblast or keratinocyte migration.

In most applications, the nanocellulose dressing will be sterilized and may also be formed into a suture, a sheet, a compress, a bandage, a band, a prosthesis, a fiber, a woven fiber, a bead, a strip, a gauze or combinations thereof. The nanocellulose dressing may also include a portions that is self-adhesive and/or an adhesive backing. The wound dressing may be a non-allergenic, multi-ribbon microbial cellulose substrate formed into a dressing that is molded to fit a specific wound site. In one embodiment, the present invention also includes a solid biocompatible implant that is a non-allergenic, multi-ribbon microbial cellulose substrate, wherein the implant is formed into a suture, a sheet, a compress, a bandage, a band, a prosthesis, a fiber, a woven fiber, a bead, a strip, clasp, prosthesis, catheter, screw, bone plate, pin, a bandage or combinations thereof. The nanocellulose may also be made from two or more different types of nanocellulose.

The implanted nanocellulose substrate may be consumed partially or totally at the site where it is implanted or surrounded by new tissue. Nanocellulose is a native biopolymer system with wide immune acceptance that may be molded into a wide variety of shapes, sizes, thicknesses, layers and the like. In fact, the nanocellulose may be manipulated during or after manufacture to create specific nanostructures formulated for the site of implantation. One example is the formation of a nanocellulose from dissolved, reprecipitated celluloses such as Nematic Ordered Cellulose, any regenerated nanocellulose, so long as the nanostructure can be arranged and generated that offers maximal response from the cells involved with skin regeneration, e.g., fibroblast, stem cells, hair follicles and keratinocytes.

The fibrous organic substrate may be a microorganism-produced nanocellulose, e.g., a member of the genus *Acetobacter* (now referred to as Gluconoacetobacter); a cellulose derivative such as carboxymethylcellulose, methylcellulose, hydroxyethylcellulose, hydroxypropylcellulose, hydroxypropylmethylcellulose and derivatives or combinations thereof, e.g., layered or stacked membrane(s). In certain embodiment the substrate is optically transparent, optically opaque, optically translucent, may change its opacity characteristics, e.g., in the presence of water, solvents or combinations thereof, permanently, reversibly or temporarily. The substrate may be nanocellulose that is wet, partially wet, dry, anhydrous, hydrated, coated or uncoated at a submicron thickness.

The wound dressing of the present inveinton will fain particular use in the treatment of chronic wounds, ulcers, facial masks and other wound sites. Furthermore, the non-allergenic nanocellulose wound dressings of the present invention may be used for the treatment of all types of wounds, e.g., those caused by laser surgery, chemical burns, cancer treatments, biopsy excision sites, scars from pathogens, entry wounds, cosmetic surgery, reconstructive surgery and the like.

BRIEF DESCRIPTION OF THE DRAWINGS

For a more complete understanding of the features and advantages of the present invention, reference is now made to the detailed description of the invention along with the accompanying figures and in which.

DETAILED DESCRIPTION OF THE INVENTION

Figure 1:
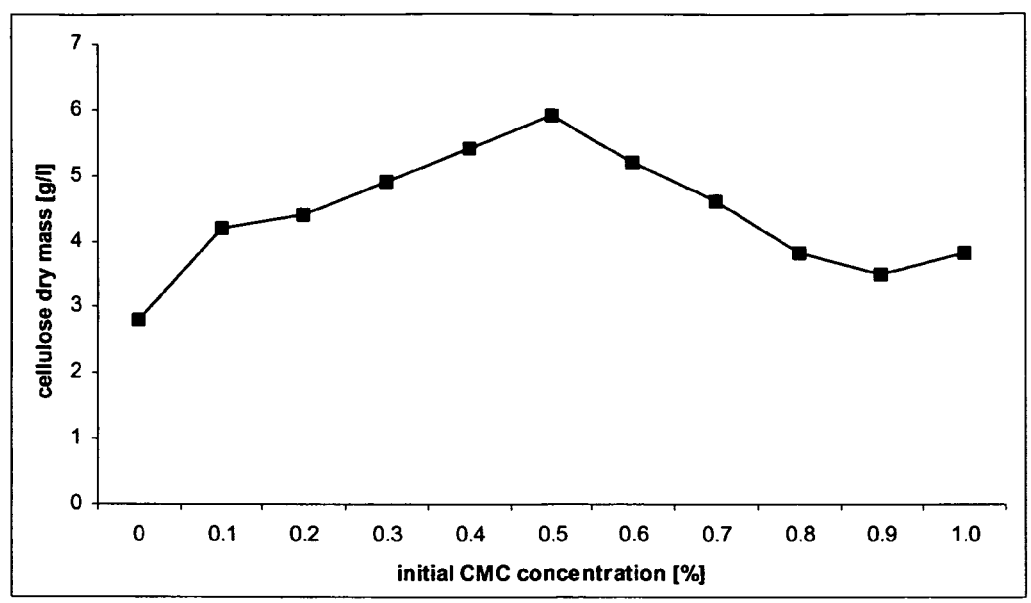
FIG. 1 Effect of different CMC concentrations in the medium on nanocellulose synthesis yield in agitated culture.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

One application of this system relates to the development of novel wound healing dressings that can be placed on the surface of the wound or into the wound bed. This new wound healing system would have the capacity to augment the effective regeneration of new tissues in situ in the body.

As used herein, the term "nanocellulose" is used to describe an architectural form of cellulose ribbons synthesized by specialized strains Acetobacter in which the ribbons are parallel to one another in bundles of varying sizes and orientations. In contrast, "non-multiribbon cellulose" commonly known as "microbial cellulose" is made up of single ribbons of cellulose that are synthesized in multiple directions both two dimensionally and three dimensionally by wild-type Acetobacter. At the three dimensional level, nanocellulose can be defined as having a principle major axis of orientation with respect to the gas-liquid interface (where it is synthesized), e.g., it is primarily parallel to the gas-liquid axis, thereby forming stratified layers of cellulose. These stratified layers can form during times inactivity or lowered activity or limited nutrient supply, etc., but they do form and are characteristic and unique to nanocellulose. Strains which form nanocellulose have the characteristic mode of reversal in the direction of ribbon synthesis from a single cell, thereby forming the strands parallel to the gas-liquid interface. A characteristic result of the ribbons being parallel to one another in bundles of varying types during synthesis is that nanocellulose has H-bonding in between parallel ribbons and makes the material stronger than non-reversal or non-multiribbon cellulose.

Furthermore, nanocellulose may also be a derivatized form of cellulose such as cellulose nitrate, acetate, carboxymethylcellulose, etc. Nanocellulose also includes any form of native crystalline cellulose, which includes not only the native crystalline form (called cellulose I, in its alpha and beta sub allomorphs, all ratios, whether pure alpha or pure beta) so long as it has the characteristic ribbons that are parallel to one another in bundles of varying sizes and orientations. Nanocellulose for use with the present invention also includes all processed crystalline celluloses, which deviates from the native form of cellulose I, such as cellulose II (which is are precipitated crystalline allomorph that is thermodynamically more stable than cellulose I). Nanocellulose includes all variations of molecular weights ranging from the lowest (oligosaccharides, 2 k-50 glucan chains linked in the β-1,4 linkage), low molecular weight nanocelluloses with a degree of polymerization (dp), which is the number of glucose molecules in the chain, of 50 to several hundred, on up to the highest dp celluloses known (e.g., 15,000 from some Acetobacter strains, to 25,000 from some algae). The present invention may also use all variations of non crystalline nanocellulose, including but not limited to, nematic ordered cellulose (NOC).

If other compounds are introduced into the nanocellulose, this is termed, "augmented nanocellulose," which can be used in either a surface or integrated application.

One example of microorganisms that produce a nanocellulose include members of the genus Acetobacter (now referred to as Gluconoacetobacter) or bacteria, microorganisms or organisms or tissues that have been transformed (permanently or transiently) with one or more genes capable or required for manufacturing cellulose and strains or sub-strains related to or derived therefrom. The nanocellulose may be a cellulose derivative, such as carboxymethylcellulose, methylcellulose, hydroxyethylcellulose, hydroxypropylcellulose and hydroxypropylmethylcellulose or combinations thereof. The fibrous organic substrate may be a microfibrillar cellulose that is wet, partially wet, dry, anhydrous, hydrated, coated or uncoated at a submicron thickness.

As used herein, the term "wound" is used to refer broadly to injuries to the skin and subcutaneous tissue initiated in different ways (e.g., pressure sores from extended bed rest and wounds induced by trauma) and with varying characteristics. Wounds are generally classified into one of four grades depending on the depth of the wound: Grade I: wounds limited to the epithelium; Grade II: wounds extending into the dermis; Grade III: wounds extending into the subcutaneous tissue; and Grade IV (or full-thickness wounds), which are wounds in which bones are exposed (e.g., a bony pressure point such as the greater trochanter or the sacrum). As used herein, the term "partial thickness wound" refers to wounds that encompass Grades I-III; e.g., burn wounds, pressure sores, venous stasis ulcers, and diabetic ulcers. As used herein, the term "deep wound" is used to describe to both Grade III and Grade IV wounds.

As used herein, the term "chronic wound" refers to a wound that has not healed within 30 days.

As used herein, the term "implanted" is used to describe the positioning of the nanocellulose substrate in the wound," e.g., by contacting some part of the wound with the substrate. As used herein, the term "integrated" is used to describe the temporary, semi-temporary, semi-permanent or permanent integration of the nanocellulose structure as part of the healed portion of a wound. The nanocellulose substrate can become semi- or permanently integrated as part of the final healed site because it is non-immunogenic. In some forms, the nanocellulose serves as a scaffold for the migration and growth of new cells at the wound site during and even after the entire healing process if the nanocellulose substrate is allowed to remain. Generally, at least part of the nanocellulose substrate will remain in the wound site as it becomes an integral part of the scar tissue.

As used herein, the phrases "promote wound healing," "enhance wound healing," and the like refer to either the induction of the formation of granulation tissue of wound contraction and/or the induction of epithelialization (i.e., the generation of new cells in the epithelium) by the implanted bacterial nanocellulose substrate of the present invention.

As used herein, the phrase "wound fluid contents" refers to liquid associated with a wound, as well as active agents that may aid in the removal of infectious agents, enhance the healing process, reduce swelling and the like. Examples of bioactive agents that may be implanted before, during or after implantation of the nanocellulose substrate or dressing include, e.g., cells, cell factors, ions, macromolecules, peptides, proteins, lipids, carbohydrates, extracts, steroids, non-steroidal anti-inflammatory drugs (NSAIDs), growth factors, antibodies, etc.

As used herein, the term "keratinocyte" refers to cells that produce keratin (ceratin), a scleroprotein or alburninoid. Generally speaking, keratinocytes are found in the epidermis or from cell lines derived from keratinocytes (e.g., bacterial derived products). The term "subject" refers to both humans and animals.

As used herein, the terms "vessel," "enclosure," "compartment," and the like refer broadly to any container capable of confining a cell-coated solid support within a defined location while allowing cellular factors to exit the enclosure into the wound and wound fluid contents to enter. If the enclosure is a sterile mesh pouch constructed of a woven, medical-grade polyester mesh, e.g., a degradable enclosure. In addition, the present invention contemplates the use of an enclosure constructed from nanocellulose membranes. The bacterial nanocellulose substrate may be manufactured on, within or about a solid support onto which the cells are grown and the nanocellulose deposited (e.g., growing on the surface of the surface of the solid support or within the solid support) is placed within the enclosure, the enclosure is sealed so as to prevent the solid support from exiting the enclosure. Generally, openings and media are provided for transporting cellular factors necessary-for nanocellulose manufacture.

As used herein, the term "substrate," or "solid support" refers broadly to any support that allows for cell growth, including, but not limited to, microcarrier beads, gels, and culture plate inserts, such as trays, grids, corrugated surfaces of any material, size or shape that permits the formation of a gas-liquid interface. Microcarrier beads suitable for use with the present invention are commercially-available from a number of sources, including Sigma, Pharmacia, and ICN. For example, the nanocellulose may be grown into a sheet that is then coated with collagen and then keratinocytes are loaded onto the substrate. In fact, under certain circumstances the nanocellulose and then the keratinocytes may be grown in the same vessel, which may even be used for shipping the final product. Culture plate inserts (i.e., cell support matrices that generally include a membrane that supports cell growth) are commercially available from, e.g., Costar, ICN, and Millipore.

The following is a brief overview of the commercialization potential of microbial cellulose for wound care products. The first efforts to commercialize microbial cellulose on a large scale were initiated by Johnson & Johnson in the early 1980's. This company pioneered in exploratory investigations on the medical application of microbial cellulose in the treatment of different types of wounds [12, 13]. However, no data of any clinical trials involving use of microbial cellulose as a wound dressing has ever been published according to our knowledge. The Johnson & Johnson Company did not launch any commercial product out of their inventions, most probably due to the problems with the development of an efficient, large-scale fermentation system. This critical factor of efficiency in the production technology still seems to play a major role for any potential company wanting to commercialize microbial cellulose for any type of product. A Brazilian company, BioFill Produtos Bioetecnologicos (Curitiba, PR Brazil) independently investigated the unique properties of cellulose biopolymer and created a new wound healing system based on microbial cellulose produced by *Acetobacter* [5, 14, 15]. Their line of products includes the following: Biofill® and Bioprocess® (used in the therapy of burns, ulcers as temporary artificial skin), and Gengiflex® (applied in treatment of periodontal diseases) [16]. According to manufacturers, differences in the technology of manufacturing involve: variable initial concentrations of carbon sources, SN ratios (surface/volume), and extended times of fermentation. Biofill® is produced within 2 days, whereas Gengiflex®, which is much thicker, requires 8 days of fermentation [16]. U.S. Pat. No. 4,912,049 protects the company's technology of cellulose film preparation.

Microbial cellulose commercial production was intensively investigated in the 1990's by several, major Japanese companies and national government organizations which set up interdisciplinary research programs with major aims to develop efficient mass production techniques. The venture was called Biopolymer Research Co., Ltd and was supported by the Japan Key Technology Center, a joint organization under MITI (Ministry of International Trade and Industry) and the Ministry of Post and Telecommunications, together with six private companies: Ajinomoto, Shimazu Construction, Nikki, Mitsubishi Paper, Nikkiso and Nakamori Vinegar [17]. The well-funded project (approximately $ 45 million)

resulted in several patents and publications, but to our knowledge, it has not yet succeeded commercially, with the exception of audio speakers from microbial cellulose by Sony [2].

Also in 1990's, intensive fundamental and applied studies on cellulose biosynthesis were undertaken at the Technical University of Lodz in Poland. The governmental support by the Ministry of Scientific Research and Information Technology endorsed the production of different types of microbial cellulose wound dressings. In addition, this led to the initiation of clinical trials on humans, and these are still successfully ongoing [7]. Furthermore, this research has produced a particularly efficient strain of *Acetobacter* [18] which grows on an inexpensive, relatively simple nutrient medium. The general failure of a large scale commercialization effort for microbial cellulose seems to have been mainly caused by the lack of an efficient fermentation system. Unlike other microbial polysaccharides which can be synthesized economically in large stirred tank fermenters, microbial cellulose must be grown in static, non-agitated cultures. Sheer stresses in agitated fermenters always damage the cellulose during synthesis. Another scale-up approach has been based on a combination of stationary and agitated culture and takes place in horizontal fermenters where optimal conditions for media supply and cell attachment to the surface of rotating discs or roller are created [20, 21].

In 1996, another company, Xylos, a US based corporation, negotiated exclusive licensing agreements with Johnson & Johnson to use their patents on cellulose based wound-care products. Since that time, the company developed its own improved manufacturing technology and was able to successfully obtain FDA approval on its products. The XCell® family of wound care products offered by the company includes XCell® Cellulose Wound Dressing and XCell® Antimicrobial Wound Dressing that have been marketed in the U.S. since 2003 [22]. In its strategy, Xylos Co. is first concentrating on the rapidly growing field of chronic wound care. According to the manufacturer, XCell® is specifically engineered and characterized by a dual-functionality of hydration and absorption to maintain the ideal moisture balance required for the good healing process [22]. A key distinction between the nanocellulose of the present invention and previously made microbial cellulose structures are the strength of the nanocelllulose as compared to currently manufactured microbial cellulose, such as that made by Xylos, Corp.

Besides the efforts to commercialize microbial cellulose for strictly medical purposes, two U.S. based companies: Cetus Co. (Emeryville, Calif.) and Weyerhaeuser Co. (Tacoma, Wash.) used a deep tank fermentation technique and patented, genetically improved *Acetobacter* strain that was able to synthesize cellulose in agitated culture, to create a product called Cellulon® with application as a food stabilizer and thickener [23]. In the mid-90', Kelco., Inc. (U.S.) has purchased the microbial cellulose business from Weyerhaeuser, and launched the product called PrimaCel® aimed to food industry.

Microbial cellulose as a wound healing system. Healing of skin wounds is a complex process which requires involvement of many different tissues, cell types and matrix components [24, 25]. There are three major directions in which wound-healing research is aimed presently [25]: (a) improvement of wound healing by elements which may potentially accelerate healing and reduce scarring; (b) development of novel skin substitutes as equivalents of autograft skin; and, (c) identification of signals that trigger the process of healing by regeneration rather than repair (scar formation). The present status of modern wound healing systems generally requires that materials used for the wound cover should create an optimal environment for epidermal regeneration by providing a barrier against wound infection and fluid loss. Many different biological and synthetic wound dressings have been developed in order to treat surgical and non-surgical lesions [25, 26, 27, 28, 29, 30]. Some of these have been quite successful in wound closure, however a search for the ideal wound dressing material is still continuing. According to modern approaches in the field of wound healing, an ideal wound dressing system must display similarity to autograft skin, both structurally and functionally [25, 31]. Table 1 shows the set of requirements to be fulfilled by a modern, successful wound care dressing material.

Clinical performance of microbial cellulose wound dressing. There have been several publications and reports on successful use of microbial cellulose as a medical product. In 1990, Fontana et al. [5] first reported the application of cellulose pellicles of varying thickness, produced by *Acetobacter*, as temporary skin substitutes. The product, called Biofill®, has been used for several skin injury treatments such as basal cell carcinoma/skin graft, severe body burns, facial peeling, sutures, dermabrasions, skin lesions, chronic ulcers, and both donor and receptor sites in skin grafts [5]. According to Farah, the thickness of the film was adjusted using the following variables: concentration of carbon and nitrogen sources in the culture medium, temperature, and fermentation time. The final product of biosynthesis was dehydrated while stretched [14].

Chronic wounds such as venous leg ulcers, bedsores, and diabetic ulcers are difficult to heal, and they represent a significant clinical challenge both to the patients and to the health care professionals. The treatment of chronic wounds involves application of various materials (hydrocolloids, hydrogels, biological or synthetic membranes) which provide a moist wound-healing environment that is necessary for optimal healing [32]. Wound dressings play an important role in the entire management of these types of wounds, and recent reports on applications of microbial cellulose dressings in the treatment of chronic wounds suggest that it displays properties superior to other existing wound-healing materials. Mayall et al. [33] used a Biofill® skin substitute in the treatment of trophic ulcerations of the limbs and showed that this material was very effective by shortening the cicatrisation time, contamination, and reducing the cost of treatment. According to Farah [14], the film applied on the lesion region with a loss of epithelial tissue acts as a new skin, eliminating pain symptoms (by isolating the nerve ending) and enhancing absorption of wound exudates. According to Fontana et al. [5] advantages of using Biofill® as a biological dressing have been confirmed in more than 300 treatments. The authors mentioned the following advantages: immediate pain relief, good and close adhesion to the wound bed, good barrier against infection, easiness of wound inspection, faster healing, improved exudates retention or reduced time of treatment, as well as reduced costs [5]. Rebello et al. [34] described use of Biofill® in the treatment of skin transplants sides (both donor and receptors) and reported that cicatrisation occurred upon 11 days of treatment. In clinical and histopathological studies by Wouk et al. [35] a comparison of different skin promoters was performed on animal models. Using criteria of healing quality and adhesion to the wound, they found Biofill® dressing to be the most effective among the four other tested.

The osmotic-diffusive properties of Bioprocess®—a microbial cellulose wound dressing were analyzed by Slezak et al. [36]. They measured values of the following coefficients: hydraulic permeability, reflection, and diffusive permeability and showed that the cellulose membrane is characterized by a low selectivity and is easy permeable for water and other solutions (aqueous solution of glucose, sucrose, ethanol, NaCl, KCl). The authors stated that the material might be used in the therapy of scalds and ulceration. In the report by Kucharzewski et al. [37], two methods of treating non-healing venous leg ulcers were compared. The experimental group of patients was treated with microbial cellulose wound dressing (Bioprocess®) whereas the control group was treated with Unna's boot hydrocolloid dressing, which is widely used in the therapy of these types of wounds. In the clinical procedure, microbial cellulose dressing with a thickness of 0.05 mm was applied on the clean wound with gauze pads placed on the top of the dressing. The limb was then bandaged, and sodium chloride solution poured over the bandage a few times a day in order to keep it moist all the time [37]. The membrane was changed every 7 days until the wound was completely healed. The results showed that 15 out of 27 patients of the experimental group treated with microbial cellulose were completely healed of ulcerations after 8 weeks of treatment, whereas only 4 out of 27 patients from the control group showed completely healed wounds after the same treatment times. The remaining 12 patients from the experimental group were healed within the next 6 weeks, whereas the process of healing for patients from the control group was completed after 20 weeks. Based on the results of these clinical studies, the authors concluded that microbial cellulose wound dressing was more effective in the treatment of the chronic venous leg ulcers than Unna's boot [37].

It has been generally shown that a combination of occlusive, moist wound dressings and compression bandages create the proper environment for painless autolytic debridement, improved development of granulation tissue, and accelerated re-epithelization [6]. In one of the most recent articles, Alvarez et al. [6], reported the use of microbial cellulose in the form of a hydrated membrane (Xcell®, Xylos Co.) in the treatment of chronic venous ulcers. In clinical trials based on 24 patients, microbial cellulose was more effective than a standard protocol (nonadherent cellulose acetate gauze) in the process of autolytic debridment. According to the authors, microbial cellulose created a protective, moist environment, very similar to a natural undisturbed wound protected by blister. Unlike microbial cellulose dressings manufactured by Biofill Co., the Xcell® product is claimed to have an ability to simultaneously donate and absorb moisture from the wound based on the fact that it conforms to wounded and intact skin differently [6]. According to the authors of these studies, the balance of moisture absorbance and delivery easily can be regulated by the secondary dressing used, which might either shift the whole system to absorb exudates (i.e. any absorbent material) or to deliver moisture (i.e. polyurethane film dressings). According to recent studies by Aung [38], the dressing was easy to apply and kept on the wound for seven days without changes. This researcher suggested that such procedures might allow private practice clinicians to offer wound care services within their own practice. According to Aung [38] the use of Xcell® may facilitate an easier dressing change and reduce the amount of material necessary for wound healing as well as reduce the frequency of dressing changes. All of these lead to the highly desired overall cost reduction, however in this particular case of treatment with Xcell® product, there is always a need for a secondary dressing to be used [38].

The most traumatic and complex of all skin injuries are caused by burns, and this results in an extensive damage to the various skin layers [25]. Burns are generally defined according to depth and range from 1st degree (superficial) to 3rd degree (entire destruction of epidermis and dermis). The standard protocol of burn management highlights several factors which accelerate the process of optimal healing [39, 40]: (a) control of fluid loss; (b) barrier to wound infection; (c) fast and effective wound closure, optimally with skin grafts or skin-substitutes; and, (d) significant pain relief.

In the studies by Czaja et al. [7], a new wound healing system based on regular, non-reversible microbial cellulose (MC) was clinically investigated in Poland on humans for the treatment of large area 2° A/B skin burns. The wound healing effects of never-dried microbial cellulose membranes and conventional gauze wound dressings as controls were compared in this research. These studies were preceeded by in vivo tests conducted on animal models that showed that microbial cellulose membranes were fully biocompatible and also successfully protected burn wounds from an excessive external fluid loss, thus accelerating the entire process of healing [11]. However, yield of synthesis and strength were less than the nanocellulose of the present invention. In fact, the material used and the Xylos product were very similar under SEM (data not shown). The yield of synthesis of the regular microbial cellulose was found to be half or less that the yield of the nanocellulose of the present invention. Furthermore, standard microbial cellulose strains tend to mutate in agitated culture and lose their ability to synthesize cellulose, which eliminates the yield.

The great conformability of this cellulose material has been proven during clinical trials on large number of patients [7, 41]. The microbial cellulose dressing adhered to the wound sites very well, and its physical properties allowed an excellent molding to all facial contours, displaying a high degree of adherence even to the moving parts (such as eyelids, nose, mouth, etc). Due to the problems with use of occlusive dressings on facial burns, the open technique using topical antibiotics is still the standard procedure. In the studies by Czaja et al. [7] a complete closure of the wounded face with a single sheet of microbial cellulose (original size 40×60 cm) has been achieved. In comparison, most of the commercially available skin substitutes usually are too small, thus two or three sheets attached to each other with staples must be normally applied. The applied, never-dried cellulose membrane allowed both: (a) maintenance of a proper moist environment around the wound; and, (b) due to its highly nano-porous structure, absorbance of the wound's exudates [7, 41].

Another interesting and important advantage of the microbial cellulose dressing includes its transparency or translucency, which allows for continuous clinical observation of the healing progress. Generally, the studies showed that microbial cellulose membranes significantly facilitated the process of necrotic debris removal (autolytic debridement), improved the development of granulation tissue, and accelerated the entire process of re-epithelialization, in comparison with the control group of patients [7]. A significant decrease in daily wound care needs, degree of pain, and the overall time of healing were observed in the treatments with microbial cellulose dressings in comparison with the control procedures.

Microbial cellulose has a unique 3-D nanostructure. For example, a microbial cellulose membrane virtually replicates the wound surface at the nano-scale level and create optimal moist conditions for wound healing and skin regeneration. Microbial cellulose, either as commercial (Xcell®, Biofill®, Bioprocess®) or non-commercial products, used so far in the clinical studies on animals and humans was synthesized by different *Acetobacter* strains, and the final product had the form of either a dehydrated or a never-dried membrane. The results of all of these studies so far suggest that there is a great potential in using this type of cellulose as a wound healing system. However, several variables influence the overall production process and performance of the final biomaterial. The origin of microbial cellulose (particular *Acetobacter* strains), its detailed structural characteristic, as well as fermentation technique may be used and have a strong impact on the performance of the final product. It is well known that celluloses produced by different *Acetobacter* strains may display some significant structural differences regarding crystallinity index, $I\alpha/I\beta$ mass fractions ratio or microfibril size [10, 42]. The quality of microbial cellulose strongly depends on the *Acetobacter* strain used in the production process (different conversion ratios of glucose-to-cellulose, rate of cellulose extrusion from the cell, problems with spontaneous mutation), culture techniques and conditions employed. Also postfermentation operations on the raw materials (the degree of dehydration, physical squeezing, treatment with bases) can strongly influence the final efficacy of the material. In our opinion, the most important factors affecting the overall product performance and production cost-effectiveness are: (a) efficient strains which do not undergo mutations over the time; (b) nutrition media based on inexpensive sources of carbon and nitrogen; and, (c) efficient, large-scale fermentation processes. The final price of the biomaterial will be strongly dependent on these variables.

In contrast to these strains, methods of manufacture and limitations, the present invention takes advantage of the unique characteristics of one or more strains of non-wild type *Acetobacter* for the manufacture of non-allergenic wound care products that have higher strength, may be custom manufactured and are in the same price range for manufacture as gauze. Unlike the products described hereinabove, the present invention finds distinct advantages in cost, speed and efficiency of manufacture, biophysical, biomechanical and biochemical characteristics of the material(s), and ease of use.

In one embodiment, the nanocellulose of the present invention may be manufactured with or without culture plate inserts that may include, e.g., a permeable microporous membrane that allows free diffusion of ions and macromolecules. These enclosures may be in the shape of common band-aids or adhesive strips, but may even be produced with three-dimensional shapes, pockets or reservoirs for the addition of active agents, and the like. For example, the shape and size of a wound may be determined and the wound dressing customized for the exact site based on the measurements provided for the wound. As wound sites can vary in terms of mechanical strength, thickness, sensitivity, etc., the substrate can be molded to specifically address the mechanical and other needs of the site. For example, the thickness of the substrate may be minimized for locations that are highly enervated, e.g., the finger tips. Other wound sites, such as ankles, elbows and the like, may be exposed to higher mechanical stress and require multiple layers of the nanocellulose substrate. In one specific embodiment, the size, shape, width, specific pore/strand, active agent(s) may be obtained from the wound site, manufactured to size, shape, etc., and then delivered to the health care provider for use. As the wound heals, subsequent wound care nanocellulose matrices are delivered to fit the new conditions at the wound site. In fact, if the wound is planned by the health care provides, the wound care dressings of the present invention may be pre-manufactured and delivered to the health care provider before the procedure that creates the wound.

As used herein, the term "transplantable substrate" refers to a solid support that includes cells (e.g., keratinocytes, referred to as a "keratinocyte-substrate") that can be placed within, e.g., an enclosure. The enclosure with a cell-substrate may be placed in the wound permanently to promote wound healing.

As used herein, the term "dressing" refers broadly to the nanocellulose of the present invention when prepared for, and applied to, a wound for protection, absorbance, drainage, etc. The present invention may further include any one of the numerous types of backings are commercially available, including films (e.g., polyurethane films), hydrocolloids (hydrophilic colloidal particles bound to polyurethane foam), hydrogels (cross-linked polymers containing about at least 60% water), foams (hydrophilic or hydrophobic), calcium alginates (non-woven composites of fibers from calcium alginate), and cellophane (cellulose with a plasticizer).

As used herein, the term "biocompatible" means that there is minimal (i.e., no significant difference is seen compared to a control), if any, effect on the surroundings of the location where the present invention is placed. For example, in some embodiments of the present invention, the nanocellulose may also include a biocompatible membrane; the membrane itself has a minimal effect on the cells of the solid support (i.e., it is non-toxic and compatible with keratinocyte growth) within the membrane and on the subject (i.e., it has no adverse impact on the subject's health or the rate of wound healing) after the enclosure is placed into a wound. The nanocellulose of the present invention does not cause an immune reaction when properly manufactured, prepared, washed and stored.

As used herein, the term "matrix" refers broadly to material for supporting cell growth. The present invention may be used as a matrix for the inclusion of a wide variety of agents that promote wound resolution, e.g., peptides, proteins, glycoproteins, proteoglycans, lipids, small molecules and even complex carbohydrates. The bacterial nanocellulose matrix may even be used as an insert on which cells (e.g., keratinocytes) are plated before implantation and integration.

One primary goal in the treatment of wounds is to achieve wound closure. Examples of cutaneous wounds include burn wounds, neuropathic ulcers, pressure sores, venous stasis ulcers, and diabetic ulcers. Open cutaneous wounds heal routinely by a process that includes six major components: (1) inflammation; (2) fibroblast proliferation; (3) blood vessel proliferation; (4) connective tissue synthesis; (5) epithelialization; and (6) wound contraction. Wound healing is impaired when these components, either individually or as a whole, do not function properly. Numerous factors can affect wound healing, including malnutrition, infection, pharmacological agents (e.g., actinomycin and steroids), diabetes, and advanced age.

Wounds that do not heal readily can cause the subject considerable physical, emotional, and social distress as well as great financial expense. Wounds that fail to heal properly and become infected often require excision of the affected tissue. A number of treatment modalities have been developed as scientists' basic understanding of wounds and wound healing mechanisms has progressed.

The most commonly used conventional modality to assist in wound healing involves the use of wound dressings. In the 1960s, a major breakthrough in wound care occurred when it was discovered that wound healing with a moist occlusive dressings was, generally speaking, more effective than the use of dry, non-occlusive dressings. Numerous types of dressings are now in routine use, including films (e.g., polyurethane films), hydrocolloids (hydrophilic colloidal particles bound to, e.g., a polyurethane foam), hydrogels (cross-linked polymers containing about at least 60% water), foams (hydrophilic or hydrophobic), calcium alginates (non-woven composites of fibers from calcium alginate), and cellophane (cellulose with a plasticizer). Unfortunately, certain types of wounds (e.g., diabetic ulcers, pressure sores) and the wounds of certain subjects (e.g., recipients of exogenous corticosteroids) do not heal in a timely manner (or at all) with the use of such dressings.

The present invention is based on a totally natural biopolymer, nanocellulose, that may be manufactured naturally or synthetically. One distinct advantage of the present invention is that is has been found to be non-allergenic. Furthermore, the nanocellulose of the present invention is very moldable or has great conformability, which other materials available today lack. Furthermore, the nanocellulose of the present invention is much stronger than commonly manufactured cellulose made by wild-type *Acetobacter*, has more controlled strand orientation, strand thickness and three dimensional structures than wild-type bacterial cellulose. Also, the present invention also uses one or more strains of *Acetobacter* that are combined to manufacture matrices of varying nanocellulose strands, which may be brought together to form nanocellulose of varying layers, levels and controlled three dimensional structures.

It has been found that the nanocellulose of the present invention has a much finer nanostructure that is responsible for inducing wound healing, cell growth and consequently skin production. While in no way limiting the invention, the present invention may initial results do suggest that fibroblasts and kerotinocytes (see, e.g., http://www.biomed.metu.edu.tr/courses/term_papers/OyaAkcelik.htm for a general discussion on these cells as they are responsible largely for new skin formation). Thus, the goals in wound healing are to stimulate such cells into forming skin. In third degree wounds, all of the skin is lost. Therefore, the kerotinocytes and other cells have to invade the wound site from outside where there was no burn wound, or in the case of extensive burns, these cells would probably have to be cultured and added along with the nanocellulose membranes. With the proper conditions, skin, without scarring, can be produced in an area where no skin exists. The present invention allows for a dramatic improvement in wound care.

A way to simulate third degree wounds in animal studies is by total excision of the skin, then follow recovery. That is what we are now doing with the porcine animal model which is known to be the best animal model most simulating human skin. So if our animal studies continue to be successful, they will help to get clinical trials for the human testing.

The nanocellulose of the present invention has been found to be extremely beneficial in the healing of first, second and third degree wounds, particularly deep secondary wounds in which there are still some remains of skin tissue for regeneration. One reason for the benefit of the present invention is that the nanocellulose matrix is extremely durable and does not break, fall-apart, open or sever even after many days at the wound site. Traditional microbial cellulose patches sever within hours or in a few days. Because of its greatly reduced cost for manufacture, strength, sustainability, non-allergenic nature and overall performance characteristics at the wound site, nancellulose most surely will be sought by professionals in the wound healing area for treatment of these types of wounds.

Nanocellulose also has the advantage that the thickness of the product can be controlled during synthesis. For example, the density of the nanocellulose microfibrils can be controlled by the innoculum size, the orientation of the microfibrils within the nanocellulose can also be controlled. Furthermore, the molecular weight of the nanocellulose, the degree of crystallinity, and the aggregation of the microfibrils into ribbons (e.g., multi ribbon patent) can be controlled and could be of considerable advantage.

Basic production of multiribbon microbial cellulose is disclosed in U.S. Pat. No. 4,954,439, issued to one of the present inventors, Dr. Malcolm Brown, Jr., relevant portions incorporated herein by reference. Briefly, a biologically pure culture of a cellulose-producing microorganism, e.g., a prokaryote is capable of making a microbial cellulose sheet during fermentation in an aqueous nutrient medium with an assimilatable source of carbon, nitrogen and inorganic substances. Certain strains are taught that provide for reversal of direction of cellulose ribbon extrusion. The reversal of direction of cellulose ribbon extrusion results on the cellulose-producing microorganism shuttling, at least periodically, first in one direction and then in the other direction along a length of an earlier-deposited cellulose ribbon to add another cellulose ribbon thereto and produce a cellulose ribbon-bundle having a width of at least two cellulose ribbons. The cellulose-producing microorganism of the present invention may be of the genus *Acetobacter, Agrobacterium, Rhizobium, Pseudomonas* or *Alcaligenes*, preferably of the genus *Acetobacter* and more preferably of the species *Acetobacter xylinum* or *Acetobacter pasteurianus*. Among preferred *Acetobacter xylinum* strains are strain NQ5, H1A; H1B; H1C; H2A; H2B; H5C; H5D; H6C; H8C; H8G; H14B; H15A; and H15B. *Acetobacter xylinum* strain NQ5, has particularly useful characteristics and has deposit No. ATCC 53582 with the American Type Culture Collection, Rockville, Md.

Unlike the basic sheet materials taught by Brown, et al., it has now been found that the manufacture and processing of the nanocellulose for preparation into the wound bed allows new cells to penetrate easily based on a native void volume or 'pore size" that is manufactured by the microbe. Native control of pore size is possible during synthesis by using additives such as sized starch granules to the medium, whereupon after synthesis, the membrane could be treated with alpha amylase to remove the starch and create the 'hole' or pore. Other examples of additives include, e.g., lactic acid, small structural proteins, nanotubes, nanosheets, nanospears, nanoparticles, and the like, proteins, carbohydrates, lipids, liposomes, antibiotics, crystals, etc. In one example, the additive is an insert that is dissolved by host proteases after insertion. In another embodiment, the additive is a bacterial nutrient or trigger that affects the characteristics of the microbial cellulose at the site by forming, e.g., a different type of cellulose. When the additive is a trigger and it is used at a specific location, e.g., lac promoter, it may trigger genes under the control of the lac promoter when exposed to β-galatosides. Also, mechanical production of pores has been used and should be cited in the claims, not limiting pore generation to this method.

Therefore, the present invention includes the addition of additives that allow for the first time to have controlled pore structure, pore spacing and/or pore size. The pore structure, pore spacing and/or pore size can be used to provide cells, active agents, gasses, minerals, vitamins, growth factors and the like at the wound site. The pore may also be left empty or even coated with materials that "soak-up" or-capture waste, debris, toxins and the like from the wound site. Furthermore, it has been found that various specific agents can be added to the implanted cellulose to expedite the wound healing process. Such agents include but are not limited to include: hyaluronan, β-1,3 glucan, carboxymethylcellulose, chitosan, various peptides and growth factors and hormones.

Using the present invention, the nanocellulose can also be designed to provide diversity in structure and functionality because before, during or even after synthesis it is possible to laminate or sandwiched the strings, sutures, sheets and/or membranes either from the same organism, or from different organisms. The manufacturing process can be applied after synthesis; however, the actual use of two or more nanocellulose manufacturing strains may be used at the same time to generate hybrid membranes of cellulose with physical features that are different from either grown alone.

Methods of cellulose molding during synthesis are taught, generally by one of the present inventors as published in EP Application No. EP0186495, which teaches a process for microbial cellulose production; relevant techniques, materials and methods incorporated herein by reference. A liquid culture of cellulose-producing microorganism and a structure are taught. The structures may be made in the presence of an oxygen-containing gas to create, if required, a gas permeable material. Otherwise, the structure is generally not gas permeable. Agents may be added during synthesis to alter the configuration of microbial cellulose. These same techniques may be applied to the nanocellulose of the present invention for the manufacture of wound dressings using the present invention.

Due to its greater strength, the nanocellulose of the present invention may also be made into sutures, sheets, dressing and the like, e.g., cylindrical shapes of nanocellulose made by growing the cellulose in tubes of silicon rubber where oxygen is easily transferred to the inner surface, the site at which the bacteria generate the cellulose. Artificial veins and arteries may be made using the present invention that may be at least semi-permanently implanted and that will generally maintain their mechanical strength before, during and after implantation and integration into the wound site. Closed chambers may be added that allow for the growth of cardiac cells and even tissues or portions of tissues that are integrated in hearts by tissue engineering with a heart-shaped nanocellulose membrane. In fact, the patient's own cells may be grown in the implant to eliminate the possibility of rejection.

While cellulose may be produced by microorganisms of the *Acetobacter, Rhizobium, Alcaligenes, Agrobacterium*, and *Pseudomonas* type (see, for example Brown, Jr., et al., J. Applied Polymer Science: Polymer Symposium (1983) V. 37 pp 33-78, relevant portions incorporated herein by reference), it is the selection and isolation of strains that manufacture nanocellulose having the specific physical properties described herein that will find the most use with the present invention. The growth of controlled nanocellulose-producing microorganisms and the production of nanocellulose occurs under carefully controlled conditions when the microorganisms are aerobically cultivated in an appropriate nutrient medium. During the formation of the nanocellulose, nutrients, oxygen content, temperature, ionic strength, pH, time, subtrate(s), shape, shaking, light and other variables may be varied to control the type, shape and thickness of the nanocellulose.

Appropriate nutrient media of the present invention generally include standard nutrient medium such as GYC which contains (g/liter of distilled water): yeast extract, 10.0; D-glucose, 50.0; CaCO3, 30.0 and agar, 25.0. Various alternatives such as replacements for glucose or yeast extract, and omissions of agar or CaCO3 are usable and well-known to those skilled in the art (Bergey's Manual of Systematic Biology, Vol. 1 pp 268-276, Krieg. ed. Williams and Wilkins, Baltimore/London (1984)). One useful nutrient medium used directly or with modifications described herein was that first described by Schramm and Hestrin (Hestrin, et al., Biochem. J. Vol. 58 pp 345-352 (1954). Standard Schramm Hestrin (SH) medium contains (g/L): D-glucose, 20; peptone, 5; yeast extract, 5; dibasic sodium phosphate, 2.7, and citric acid monohydrate, 1.15 (pH adjusted to between about 3.5 and 5.5 with HCl). When SH is used without glucose (SH-gluc), this indicates the above SH composition, but without the 10 g glucose/liter addition.

The cellulose produced by *Acetobacter xylinum* (formerly known as *Acetobacter aceti* subsp. *xylinum* and reclassified by the 1984 Bergy's Manual cited above as a subspecies of *Acetobacter pasteurianus* and *Acetobacter hansenii*) has been widely studied. In the present application the primarily studied cellulose-producing microorganism is termed "*Acetobacter xylinum*," also known as *Gluconacetobacter xylinus* subspecies *xylinus* or equivalents thereof. It is understood that these several names may be used to indicate the same organism as is the cellulose derived from related bacteria or bacteria that include the genes that are necessary to produce plant or microbial-derived cellulose. In one example, *Acetobacter* strain NQ-5 (ATCC 53582), deposited with the American Type Culture Collection (ATCC) may be particularly useful. Cellulose for use with the present invention may be made in accordance to the general teachings of U.S. Pat. No. 4,942,128, relevant portions incorporated herein by reference. Yet another strain that may be particularly useful for the present invention is *Acetobacter* strain AY-201 (23769) also available from ATCC, although this invention is not limited to any particular strain of any cellulose producing bacterium or prokaryotic organism.

EXAMPLE 1

Nanocellulose synthesized in abundance by *Acetobacter xylinum* shows vast potential as a novel wound healing system. The high mechanical strength and remarkable physical properties result from the unique nanostructure of the never-dried membrane.

Recent advances in the field of biomaterials and their medical applications indicate the significance and potential of various microbial polysaccharides in the development of novel classes of medical materials. Several of the microbially-derived polysaccharides possessing novel and interesting physical and biological properties already have been applied in biotechnology products or are presently being widely investigated (i.e. hyaluronic acid, dextran, alginate, scleroglucan). Among them, microbial cellulose, a polymer synthesized in abundance by *Acetobacter xylinum*, belongs to the most promising class of biopolymers, despite the fact that its potential of becoming a high-value product of biotechnology has not yet been fully estimated or discovered [1]. The unique physical and mechanical properties of microbial cellulose as well as its purity and uniformity determine applications which range from high-quality audio membranes [2] and electronic paper [3] to fuel cells [4] and medical materials [5, 6, 7]. This last, emerging area seems to be particularly important since many efforts have been devoted in recent years to explore new skin substitutes and modern wound dressing materials using tissue engineering approaches. Various polymeric materials recently have been investigated for wound dressing application yielding many successful outcomes, but the search for an ideal skin-graft substitute with properties and functionality similar to human skin is still continuing. The present inventors have found that microbial cellulose, while chemically the same as plant cellulose, displays novel physical properties determined by the particular genetics of the organism. In such a case, microbial cellulose has a distinctive nanofibrillar structure which may become a perfect matrix as an optimal wound healing environment.

Biosynthesis, structure and properties of microbial cellulose. *Acetobacter xylinum* is a simple Gram-negative bacterium which has an ability to synthesize a large quantity of high-quality cellulose organized as twisting ribbons of microfibrillar bundles [8]. During the process of actual biosynthesis, various carbon compounds of the nutrition medium are utilized by the bacteria, then polymerized into single, linear β-1,4-glucan chains and finally secreted outside the cells through a linear row of pores located on their outer membrane. The subsequent assembly of the β-1,4-glucan chains outside of the cell is a precise, hierarchical process. Initially, they form subfibrils (consisting of 10-15 nascent β-1,4-glucan chains), then later microfibrils, and finally bundles of microfibrils consisting of a loosely wound ribbon, which comprises of about 1000 individual glucan chains [9]. The thick, gelatinous membrane formed in static culture conditions as a result of these processes is characterized by a 3-D structure consisting of an ultrafine network of cellulose nanofibres (3-8 nm) which are highly uniaxially oriented [10]. Such a three-dimensional structure, not found in vascular plant cellulose, results in high cellulose crystallinity (60-80%) and an enormous mechanical strength. Particularly impressive is the fact that the size of microbial cellulose fibrils is about 100 times smaller than that of plant cellulose. This unique nano-morphology results in a large surface area which can hold a large amount of water (up to 200 times of its dry mass) and at the same time displays a great elasticity, high wet strength, and conformability. The small size of microbial cellulose fibrils seems to be a key factor which determines its remarkable performance as a wound healing system. Furthermore, the never-dried cellulose membrane is a highly nanoporous material that allows for the potential transfer of antibiotics or other medicines into the wound, but at the same time it serves as an efficient physical barrier against any external infection. The cellulose produced in the form of a gelatinous membrane can be molded into any shape and size during its synthesis, depending on the fermentation technique and conditions used [1]. Unlike celluloses of plant origin, microbial cellulose is entirely free of lignin and hemicelluloses. A vigorous treatment with strong bases at high temperatures allows the removal of cells embedded in the cellulose net, and it is possible to achieve a non-pyrogenic, non-toxic, and fully biocompatible biomaterial.

The present invention is based on the formation of nanocellulose and the unique properties of such materials. Knowing what is understood about the biosynthetic process, it is possible to select genetic modification of nanocellulose producing microbe strains to customize particular products that would greatly benefit from a particular physical form. For instance, the shape of nanocellulose can be determined by the shape of the fermentation vessel. Thus, if molded non-woven nanocellulose products are required, they can be synthesized according to the shape of the mold. If the pore structure of never-dried nanocellulose is to be custom synthesized, then new strains and fermentation conditions can easily be matched to produce such materials. The degree of polymerization, the crystallization, and the size and shape of the microfibrils and microfibrillar aggregates could all be controlled genetically.

EXAMPLE 2

Fibrillar alterations of nanocellulose have been previously shown to occur, for example, by ultrastructural studies using techniques such as electron microscopy (Haigler, et al., J. Cell Biology, Vol. 94 pp 64-69 (1982) and Ben-Hayim et al. J. Cell Biology, Vol. 25 pp 191-207 (1965)). Microbial production of a cellulose leads to greatly improved and/or unique macroscopic properties such as resiliency, elasticity, tensile strength, degree of water absorptivity or retention of absorptive capacity after repeated wettings.

Cellulose assembled by a static aerobic culture of Acetobacter xylinum may be contained in a hydrophilic membrane known as a pellicle. This cellulose is quite strong when wet, but brittle when dried. One of the major obstacles in using the natural absorbency of this native bacterial cellulose has been its inability to effectively retain absorbancy through cycles of wetting and drying. To improve the physical properties of the cellulose, a cellulose derivative such as carboxymethylcellulose (CMC) may be added to the culture medium during microbial synthesis of cellulose. Inclusion of CMC in the culture medium alters the produced cellulose to result in a product that retains most of its native absorbancy through cycles of wetting and drying. The physical properties of microbial cellulose product by cellulose derivatives or related substances expand the material uses of cellulose.

Cellulose is the nature's most abundant polymer composed of β-1,4 glucan chains. It has obvious uses in the textile and forestry industries. In such applications, entire cells microns in diameter are the norm for the structure of the products. On the other hand, native microbial cellulose consists of fine ribbon fibrils whose width is approximately 100 nm. The lengths of these fine fibrils can range from about 1-9 μm, and they form a dense reticulated structure (see, for example, Brown, R. M., Jr., J. H. M. Willison, and C. L. Richardson. 1976. Cellulose biosynthesis in Acetobacter xylinum: 1. Visualization of the site of synthesis and direct measurement of the in vivo process. Proc. Nat. Acad. Sci. U.S.A. 73(12):4565-4569.).

Studies on the effects of carboxymethylcellulose (CMC) on the synthesis of bacterial cellulose produced in the agitated culture by Acetobacter xylinum strain NQ5 (ATCC 53582) were conducted. The action of two independent factors, namely environmental stress occurring during agitation, and the presence of CMC in the medium, resulted in a significant structural alteration of the microbial cellulose causing a lowering of its crystallinity index as well as the I mass fraction. From these studies has emerged the concept that interesting structural characteristics and properties of such a cellulose composite, especially its well-developed surface (consisting of dispersed microfibrils) could have important properties, particularly in the pulp industry (for the process of paper finishing), or in the environmental niche, being used in bioremediation, or in the production of novel wound care dressing materials.

Cellulose synthesized by Acetobacter xylinum in the form of organized, twisting ribbons, is a highly crystalline cellulose I allomorph. The glucan chains which are extruded from the cellulose synthesizing complexes, are localized in the pores of the bacterial outer membrane and are associated outside into microfibrils and then into bundles of cellulose ribbons (Brown et al., 1992). It has been revealed using electron diffraction analyses (Sugiyama et al., 1991) and (CP-MAS) 13C NMR (VanderHart and Atalla, 1984; Yamamoto and Horii, 1993) that cellulose is a composite of two different crystalline phases called Iα and Iβ. Normally, Acetobacter xylinum cellulose displays characteristics of highly crystalline, Iα-rich cellulose (VanderHart and Atalla, 1984). However, it is known that the cellulose crystallization process can be interrupted by addition of fluorescent brightening agents or cellulose derivatives, which interact with nascent cellulose (Haigler, et al., 1980; Mondal and Kai, 2001). Recently, the structure of cellulose composites formed by the addition of different cell-wall polysaccharides and reagents, like gluco- and galactomannans (Whitney et al., 1998; Tokoh et al., 1998; Iwata et al., 1998), xyloglucan (Whitney et al., 1999), pectin (Chanliaud and Gidley, 1999) were widely investigated using X-ray diffraction, 13C CP/MAS NMR and electron microscopy techniques. Structural interactions between those polysaccharides have been studied and some interesting properties of such composites were found.

Generally, cellulose derivatives alter ribbon assembly at a higher level of organization than fluorescent brightening agents and direct dyes (Haigler, 1982). Cellulose derivatives interfere with the aggregation of cellulose microfibrils and allow them to remain separated. Yamamoto et al. (1996) found that this reduction in microfibril size induced by carboxymethylcellulose (CMC) is associated with enhanced crystallization of cellulose I$\beta$. In addition, it has been also reported that ratio of I$\alpha$/I$\beta$ cellulose content can be also easily altered by different culture conditions, e.g. different polymeric additives or temperature (Yamamoto et al., 1996; Hirai et al., 1998).

The effect of CMC was studies in the culture medium on synthesis and structural characteristics of nanocellulose produced in agitated culture by *Acetobacter xylinum* NQ5 (ATCC 53582) strain. Influence of external forces arising during agitation together with the effect of CMC addition on bacterial cellulose crystallization and accumulation has been studied using X-ray diffraction. Changes of I$\alpha$ and I$\beta$ cellulose mass fractions in modified cellulose samples were estimated using FT-IR spectroscopy. In order to examine detailed structural modifications and changes in cellulose samples, transmission electron microscopy (TEM) and scanning electron microscopy (SEM) techniques also have been applied.

Microorganisms. *Acetobacter xylinum* NQ5 (ATCC 53582) strain from the collection located in the Brown laboratory at the University of Texas at Austin, was used in this study.

Culture medium. Schramm and Hestrin (SH) medium (Hestrin and Schramm, 1954) or SH medium containing different concentrations of carboxymethylcellulose (CMC) with a degree of substitution (DS)=0.7 and a molecular weight (MW)=700,000, without pH adjustment was used in all experiments unless otherwise specified.

Culture conditions. 150 ml of (SH+CMC) medium in the Erlenmeyer flask was inoculated with a 15 ml aliquot of bacterial cells, aseptically squeezed from 3 days old cellulose pellicle, and incubated on a rotary shaker (Lab-Line Instruments, Inc. USA) operating at 120 rpm, for 7 days, at 28° C. The synthesized cellulose was separated from the medium by filtration and centrifugation. The amount of cellulose produced was measured as a dry mass of polymer after washing it in 2% sodium hydroxide (overnight) followed by three changes of distilled water in order to remove cells and medium embedded in the cellulose material.

FT-IR spectroscopy. Each cellulose sample was air-dried on a glass slide in the form of a thin film and which was then placed across a hole in a magnetic holder. FT-IR spectra were obtained using a Perkin-Elmer spectrometer (Spectrum 2000). All spectra were recorded with the accumulation of 32 scans, resolution of 2 cm-1, in the range from 4000 cm-1 to 400 cm-1, normalized using the band at 2900 cm-1 due to the COC stretching vibration. The f$\alpha$ fraction of the samples was calculated by the following equation (Yamamoto et al., 1996): f$\alpha$=2.55 f$\alpha$IR—0.32, where f$\alpha$IR of cellulose can be calculated as A$\alpha$/(A$\alpha$+A$\beta$) and A$\alpha$ and A$\beta$ are absorbencies at 750 cm-1 and 710 cm-1, respectively.

X-ray diffraction. Cellulose samples in the form of sheets dried on glass slides were placed in an X-ray holder. X-ray diffraction spectra were recorded using Ni-filtered Cu-K$\alpha$ radiation ($\lambda$=0.15418 nm) produced by either a Rigaku RINT 2200 X-ray generator equipped with a Position Sensitive Proportional Counter (PSPC) as the detector or a Philips PW 1720 X-ray generator operating at 35 kV and 25 mA, equipped with a Philips vertical scanning diffractometer and a diffracted beam monochrometer. Scans were performed over the 5-40° 2$\theta$ range using either steps 0.05° or 0.01° in width. The data were analyzed using the WinFit software program (Krumm S., 1997) or the Jade 5 XRD software program. The crystallite size was estimated by substituting the full-width at half-maximum (FWHM) into the Scherrer equation (Nieduszynski and Preston., 1970; Alexander, 1979).

Negative staining for TEM observations. A suspension of bacteria was obtained by culturing *Acetobacter xylinum* in SH medium with addition of 100 µl of Celluclast 1.5LTM from Trichoderma resei, Novo Nordisk Bioindustrials, Inc., Denmark. After 3 days of culture, cells were centrifuged, washed in phosphate buffer (pH=7.0), centrifuged again and finally, they were resuspended in a small volume of the phosphate buffer. For negative staining, a drop of cell suspension was mounted on a Formvar coated grid. The grid with cells was put on a drop of experimental medium (SH+different concentration of CMC) for the desired incubation time, washed with distilled water, 2.5% Triton, and water again, and finally stained with 2% aqueous uranyl acetate. Grids were examined with a Philips 420 transmission electron microscope (TEM) operating at 100 kV. The data were analyzed, and the measurements were carried out with the Image Pro-Plus software program (version 3.0 for Windows 95/NT, Media Cybernetics, USA) using different calibration patterns.

Sectioning for light and electron microscopy. The microbial cellulose material was fixed in 4% glutaraldehyde, washed in cacodylate buffer, and then fixed again in 2% osmium tetroxide (OsO4). After washing in distilled water, the cellulose was dehydrated in stepwise concentrations of ethanol followed by absolute acetone, then infiltrated with resin-acetone solutions. Cellulose was embedded in epoxy resin (EPON; Electron Microscopy Sciences, USA) and allowed to polymerize at 60° C. for 24 hours. Both thick (about 1 µm) and thin sections were cut on a Reichert OM2 ultramicrotome, using either a glass or diamond knife, respectively. Thick sections were stained with 1% bromotoluidine and observed with a Zeiss Universal Light Microscope. Ultra-thin sections were gently placed on the grids, stained with lead citrate, washed in 0.02N NaOH and boiled distilled water and finally post-stained with 2% uranyl acetate. Grids were then examined with Philips 420 transmission electron microscope (TEM) operating at 100 kV.

SEM observations. Cellulose samples were fixed in 4% glutaraldehyde followed by 2% osmium tetroxide and dehydrated using the same procedure as for sectioning. Samples were either freeze-dried or critical point dried (Samdri-790, Tousimis Research Corp.) and then coated with gold (30800, Ladd Research Industries, Inc.). An Hitachi S-4500 field emission scanning electron microscope operating at 10 or 15 kV was used for examination of the samples.

Mechanical testing. Mechanical properties (tensile strength, Young's modulus) of dried cellulose samples have been measured using a ZWICK 1435-type mechanical tester.

Influence of different polysaccharides additions to the culture medium on bacterial cellulose (BC) formation has been quite widely investigated recently (Yamamoto et al., 1996; Sakairi et al., 1998; Hirai et al., 1998; Tokoh et al., 1998). Particular attention has been paid to the interaction between synthesis of microbial cellulose by various *Acetobacter* strains and water-soluble cellulose derivatives added to the fresh culture medium. While *Acetobacter* cells normally synthesize tightly organized cellulose ribbons, it was reported that their incubation in the medium containing CMC results in the production of disorganized, splayed ribbons with different subunits width (Haigler, 1982). Most of those experiments have been carried out using cellulose synthesized statically, while in our experiments we investigated modified bacterial cellulose produced in the agitated culture conditions.

The present inventors have found that external forces occurring during agitation have a certain influence on the cellulose crystallization process, causing a percentage decrease of both Iα mass fraction and degree of crystallinity. Formation of characteristic cellulose spheres in the agitated culture has been also described and discussed in that paper. In the present study we examined the influence of both factors, CMC addition to the medium as well as the external, environmental stresses during agitation, on synthesis yield and formation of bacterial cellulose ultrastructure.

Figure 2:
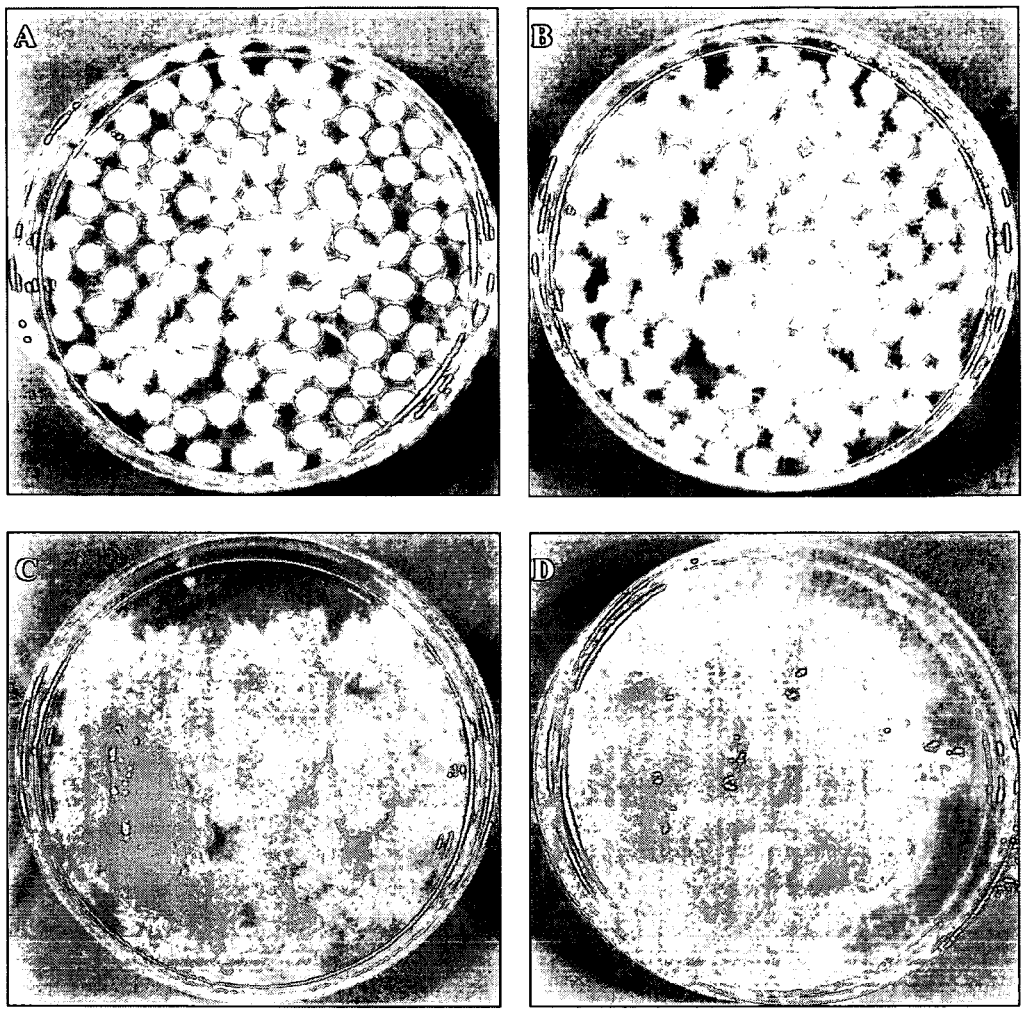
FIG. 2 Effect of CMC addition on nanocellulose sphere formation in agitated culture; concentrations of CMC added to the medium A (0.1%), B (0.2%), C (0.6%), D (1%).
Figure 3:
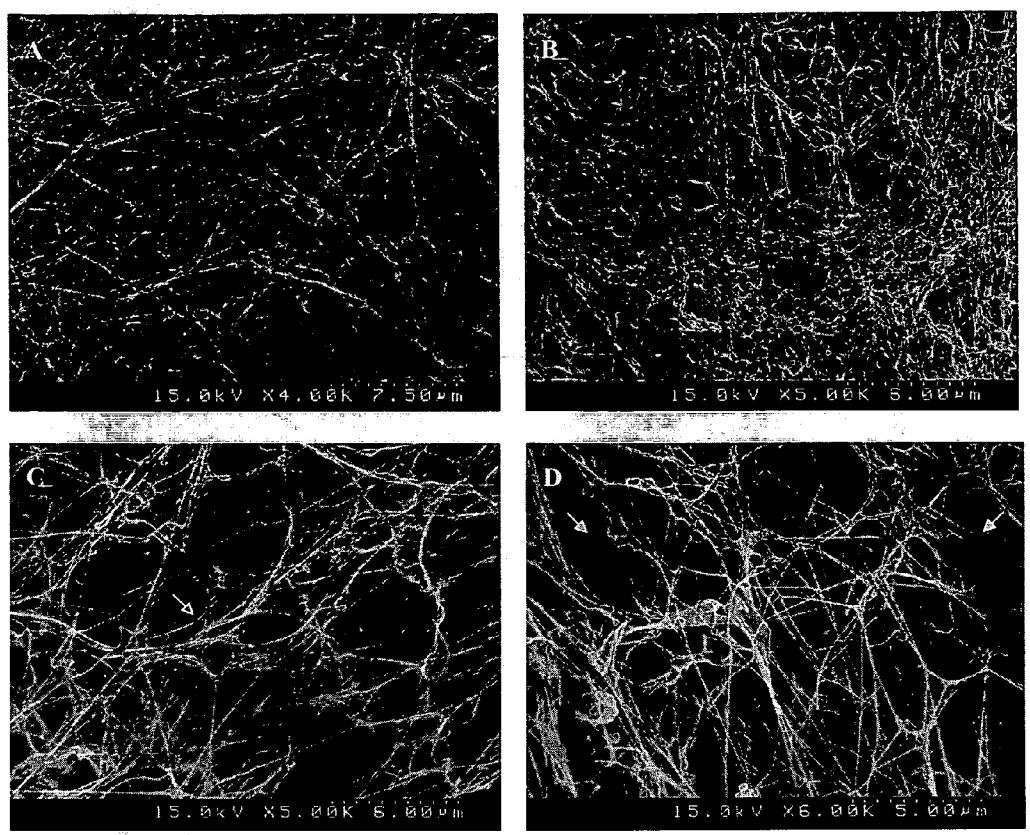
FIG. 3 Structure of bacterial nanocellulose from agitated culture modified with CMC of different concentrations: (A) 0.1%, (B) 0.6% (C) 0.8%, (D) 1.5%; arrows indicate dense, heterogeneous regions within cellulose where CMC has been trapped.

FIG. 1 shows the yield of nanocellulose synthesis in the SH medium containing different concentrations of CMC, in the range of 0.1-1% (w/v %). The increasing nanocellulose production yield reached a maximum value for the 0.5% CMC addition, where more than a twofold increase was observed. Recently, other researchers have also reported a similar significant increase in cellulose synthesis while culturing *Acetobacter* in SH medium containing CMC (Sakairi et al., 1998). In order to understand this phenomenon, Sakairi et al. (1998) concluded that CMC added to the medium might be first depolymerized and then utilized in the metabolic cycle of the bacteria. These results are reasonable considering fact of natural ability of *Acetobacter* to synthesize CMCase (β-1,4-endoglucanase), which occurs particularly efficiently during agitated culture (Watanabe et al., 1998; Tahara et al., 1997). According to Sakairi's assumptions (Sakari et al., 1998) carboxymethyleted glucose residues might be in some way re-transformed in the bacterial metabolic system to form glucose (by removing carboxymethyl groups), which eventually could be used as an additional carbon source for extracellular cellulose synthesis. The only remaining question is how much of the initial amount of CMC can be depolymerized and taken into the bacteria's metabolic cycle as well as how much will still remain bound to the cellulose microfibrils, even after the purification process. It is shown herein that a concentration of 0.5% CMC seems to be the optimal to enhance NC-CMC (=nanocellulose-CMC) composite synthesis. Increasing the concentration of CMC in the culture medium causes the nanocellulose spheres to become much more loose, forming a characteristic variety of fuzzy structures (FIGS. 2a, b) or just a cellulose gel, which occurs at the high concentrations of CMC (FIGS. 2c, d). It is known that *Acetobacter* cells synthesizing nanocellulose ribbons are subjected to the certain centrifugal forces during agitation and tend to bind together creating large cellulose spheres (Czaja et al., submitted). The loose, fuzzy structures are simply the result of synthesis of the large quantity of splayed and disorganized ribbons which are not tightly adhered together. The high CMC concentration in the medium does not result in the formation of integrated product, so a particular gel includes a single groups of ribbons can be produced by this way. Sections (data not shown) cut across the fixed and embedded fuzzy nanocellulose spheres (modified with 0.1% of CMC) revealed that in comparison with characteristic regular cells arrangement formed in the control agitated culture (data not shown), the regions of more chaotically scattered *Acetobacter* cells are seen in NC-CMC composite. Closer insight into those structures has been achieved using SEM technique. The micrographs shown in FIG. 3, demonstrate nanocellulose produced in the medium containing different CMC concentrations. Close observation has revealed some interesting structural differences. A smaller addition of CMC seams to result in no significant structural alteration so fine net of entangled, disordered and curved nanocellulose ribbons, similar to that produced in the control agitated culture (without any additional reagents) is being formed. Because the specimen has been coated with gold, it is rather difficult to discuss the hypothetic differences in the thickness of the single naocellulose microfibrils based on the SEM micrographs. The interesting altered regions of NC-CMC composites are visible in FIGS. 3c and d, where micrographs of nanocellulose modified with higher concentration of CMC are shown. Those structures display a considerable heterogeneity ranging from regions of a normal nanocellulose network to areas of nanocellulose ribbons coated by CMC which form dense layers of a NC-CMC composite (FIGS. 3c, d).

Figure 4:
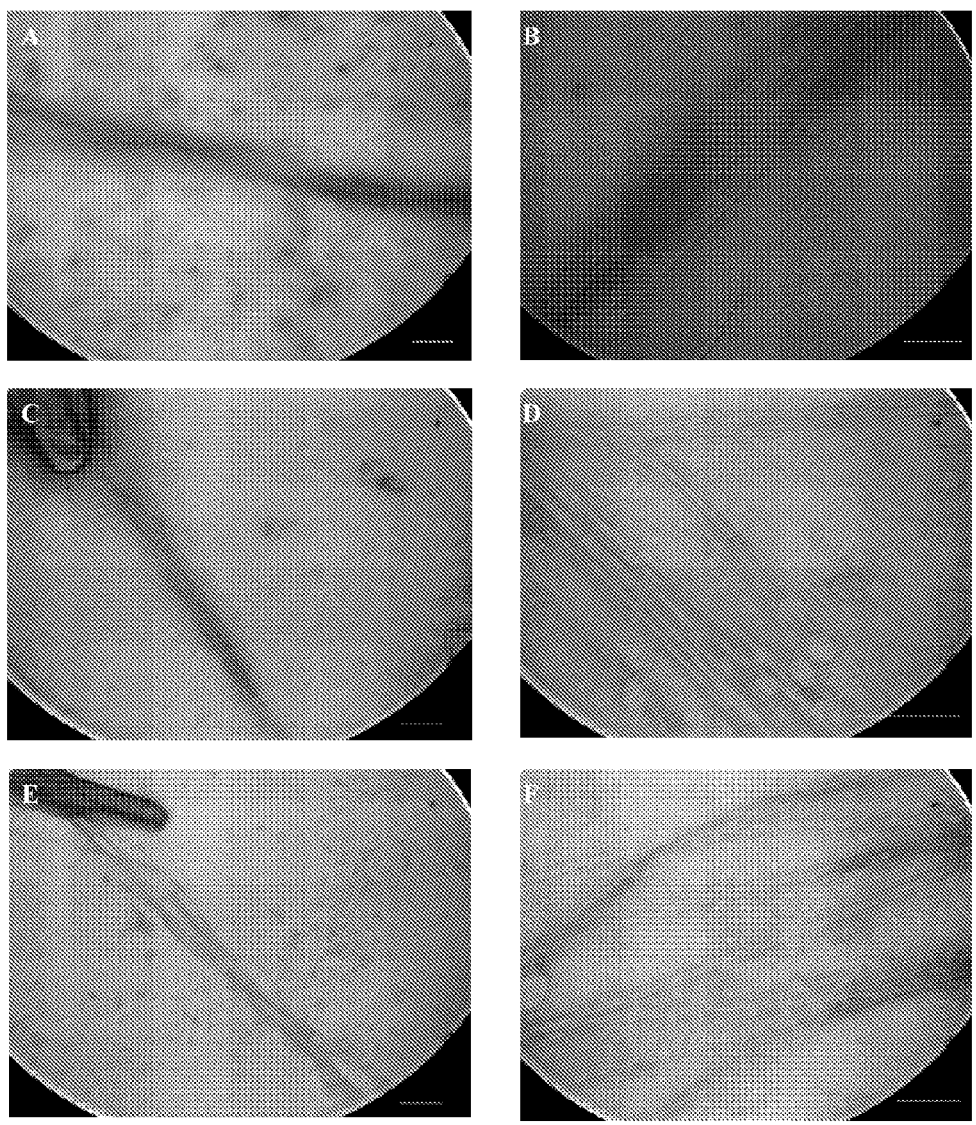
FIG. 4 TEM micrographs of nanocellulose ribbons synthesized in the presence of different CMC concentrations, (A) and (B) control-without CMC, (C) and (D) 0.5% CMC, (E) and (F) 1% CMC; scale bars: (A) 100 nm, (B) 50 nm, (C) 100 nm, (D) 30 nm, (E) 100 nm, (F) 25 nm.

In order to better visualize the structural arrangement and interactions between nanocellulose and CMC, the TEM technique has been applied. FIG. 4 shows cellulose ribbons synthesized by *Acetobacter* in the presence of different CMC concentrations. In comparison with a tight organization of cellulose ribbons observed for a cell incubated in the standard SH medium shown in FIGS. 4a and b, the formation of well-defined, separated microfibrils of widely splayed ribbons are characteristic for CMC-induced cellulose ultrastructure (FIGS. 4c-f). The tendency to synthesize more splayed and disorganized ribbons with different subunits width has been observed with increasing concentrations of CMC in the culture medium. Therefore, addition of 1% CMC into fresh SH medium resulted in its strong adhesion on the surface of microfibrils and consequently in full prevention of their further aggregation (FIGS. 4e and f). Those effects have been also reported and widely discussed by other researchers (Heigler, 1982; Hirai et al., 1998). The ranges of ribbon splaying and especially microfibrils size are dependent on CMC concentration as well as the chemical characteristics of carboxymethylocellulose used in the experiments. Haigler (1982) proved that among different types of tested CMC, the one with DS=0.7 was much more effective in inducing synthesis of loosely aggregated cellulose ribbons than the others. The different microfibril widths have been measured in our study to find a correlation between CMC concentration and distribution of synthesized microfibrils sizes. A general trend shown in our studies demonstrated that a larger quantity of small-size cellulose microfibrils has been synthesized with increasing CMC concentrations (data not shown), with fibrils of widths below 3 nm observed for *Acetobacter* cells cultured in the presence of 1% CMC, and microfibrils above 7 nm observed for 0.1% CMC. Such a tendency is in a quite good agreement with results previously reported by Hirai et al. (1998), who demonstrated that average size of cellulose fibrils decreases with increasing concentration of CMC. Microfibrils sizes reported in that paper ranged from 14 nm to 6 nm in width.

Figure 5:
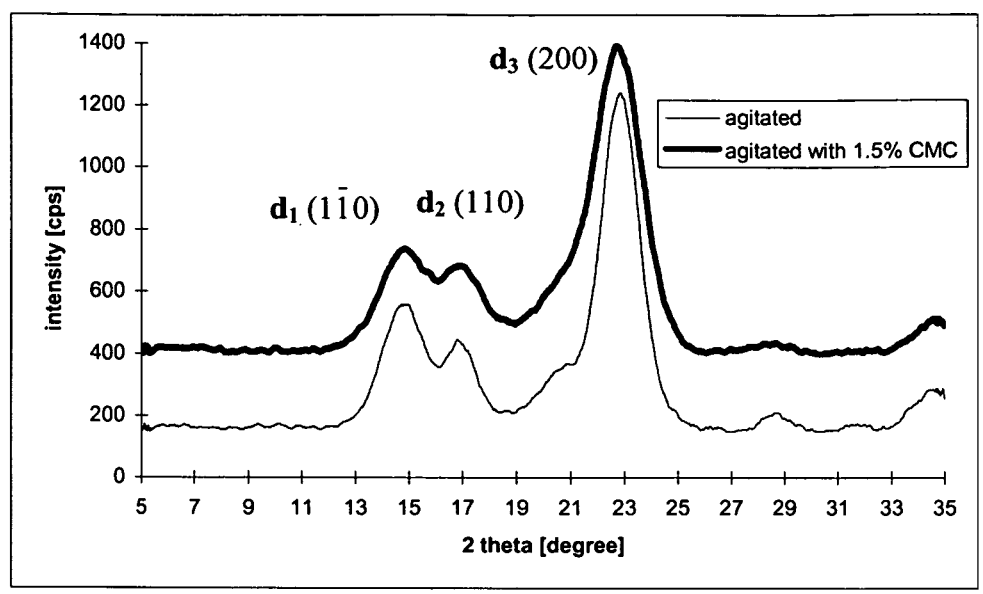
FIG. 5 X-ray diffractograms of bacterial nanocellulose samples. Three typical diffraction peaks occurring in the region of 10-25° are labeled as $d_1$, $d_2$, and $d_3$.

The structural organization of NC-CMC composites produced in agitated culture also has been examined using X-ray diffraction and FT-IR technique. As previously reported (Czaja et al., submitted) conditions of stress occurring during agitation resulted in the structural changes of bacterial cellulose ultrastructure, decreasing its degree of crystallinity and Iα mass fraction. Addition of carboxymethylocellulose to agitated culture of *Acetobacter* might be considered as another disturbing factor in the entire process of cellulose ribbon arrangement. The question is how these two independent external factors can affect the cellulose structure and especially its Iα/Iβ mass fractions ratio. FIG. 5 demonstrates X-ray diffractograms of nanocellulose from agitated culture with and without addition of 1.5% of CMC. Comparison of 2θ angle values revealed that in case of NC-CMC composite, the (1$\bar{1}$0)- and (110) reflections are positioned closer together than the same reflections for X-ray patterns of the control cellulose. Changes in the d-spacings shown in Table 1 are considered to represent a different proportion of Iα and Iβ cellulose allomorphs as reported previously (Watanabe et al., 1998; Yamamoto et al., 1989; Czaja et al., submitted). The crystallite sizes estimated for (1$\bar{1}$0) and (110) diffractions seem to be almost the same for both analyzed cellulose samples, although a slight difference has been revealed for diffraction (200), where the crystallite size value of 6.4 nm has been determined for NC from control-agitated culture and 6.0 nm for NC-CMC composite. Considering our findings and results obtained by Yamamoto et al. (1996) and Watanabe et al. (1998), such a decrease in crystallite size should be in a good agreement with the general trend which demonstrates that cellulose microfibril size decreases during synthesis in specifically altered culture conditions (stationary→agitated→agitated with CMC addition). A comparison of X-ray data and TEM data shows that the estimated crystallite sizes using the Scherer equation (Nieduszynski and Preston, 1970) are in pretty close correlation with the cellulose microfibrils sizes determined from TEM measurements.

TABLE 1 d-spacings, crystallite sizes and percent crystallinity of nanocellulose samples determined from X-ray diffractograms.

| CELLULOSE SAMPLE | d-spacings [Å] | | | Difference in 2θ angle (peak 1 – peak 2) | crystallite sizes [nm] | | | percent crystallinity c [%] |
|---|---|---|---|---|---|---|---|---|
| | $d_1$ | $d_2$ | $d_3$ | | $cr_1$ | $cr_2$ | $cr_3$ | |
| agitated | 5.9 | 5.17 | 3.83 | 2.15 | 7.9 | 6.6 | 6.4 | 84 |
| agitated with 1.5% CMC | 5.97 | 5.24 | 3.83 | 2.07 | 8.0 | 6.7 | 6.0 | 79 |

Figure 6:
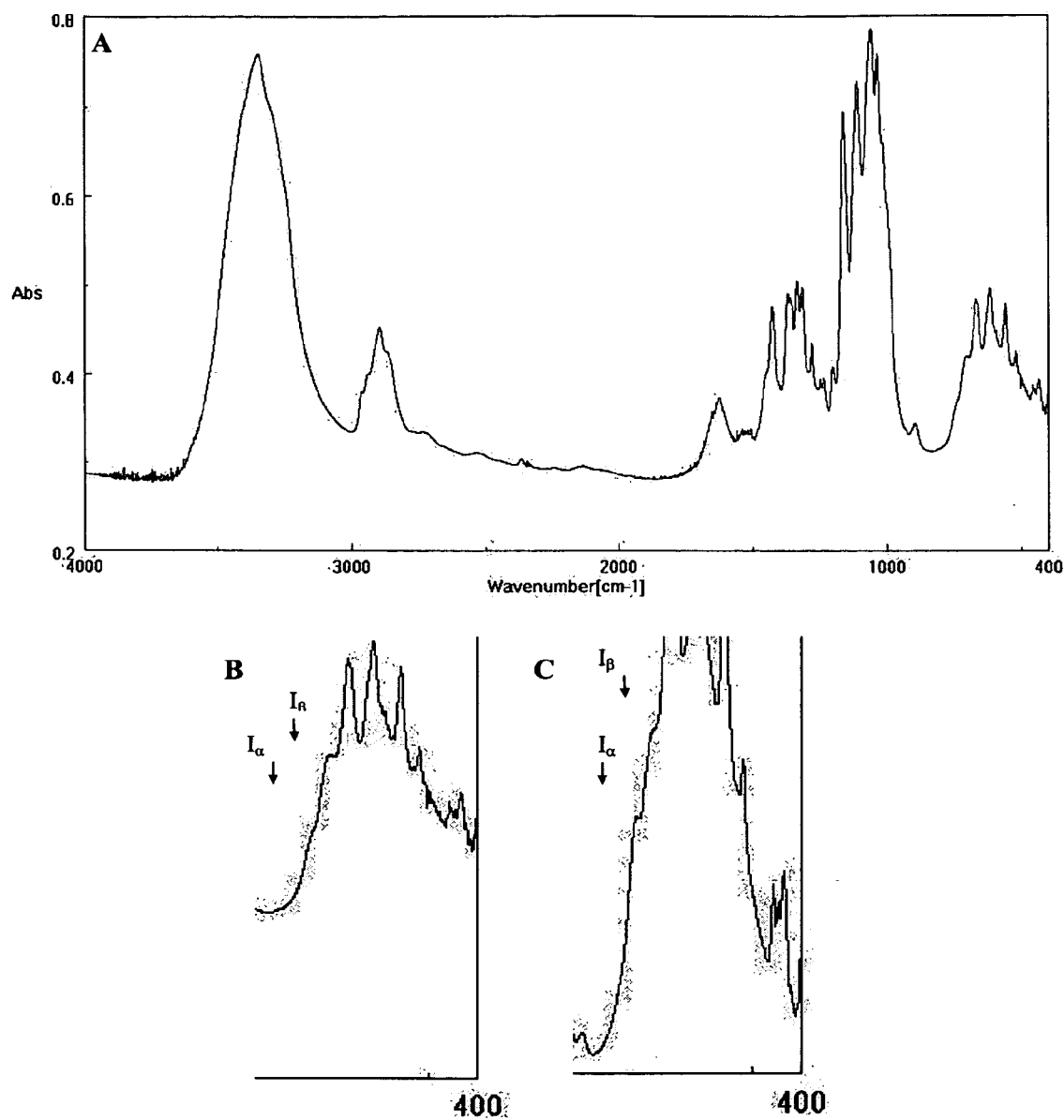
FIG. 6 FT-IR spectrum of bacterial nanocellulose produced in agitated culture in the presence of 1.5% CMC (A); region with peaks corresponding to $I_\alpha$ and $I_\beta$ cellulose mass fractions has been enlarged (B) and compared with analogical region of spectrum for cellulose synthesized in agitated culture without CMC addition (C); arrows correspond to $I_\alpha$ (750 cm$^{-1}$) and $I_\beta$ (710 cm$^{-1}$) mass fractions.

In order to examine that effect more specifically, FT-IR spectroscopy was applied. The spectrum shown in FIG. 6a revealed that CMC addition resulted in a decrease of the Iα cellulose mass fraction. Careful observations of the enlarged regions with peaks assigned to Iα and Iβ cellulose mass fraction reveal several interesting differences. While the peak corresponding to the Iα allomorph (750 cm-1) in the spectrum obtained from nanocellulose synthesized in the control agitated culture (without CMC additives) is quite well defined, a significant reduction in the intensity for the analogical peak in case of the NC-CMC composite can be clearly seen (FIGS. 6b, c). A similar effect concerning peak intensity reduction also has been reported recently by Tokoh et el. (1998) who cultured Acetobacter cellulose in the presence of acetyl glucomannan. Using a previously proposed formula (Yamamoto et al., 1996) the cellulose Iα mass fraction has been determined from FT-IR measurements for modified cellulose samples. The interesting trend can be observed considering the results in Table 2, which show structural characteristics of cellulose samples synthesized in different culture conditions. A gradual decrease both in Iα mass fraction and the crystallinity index can be observed between the stationary and agitated culture additionally disturbed by CMC addition. These results taken together with our data from TEM analysis confirm that Iα cellulose fraction probably is much more frequently crystallized in larger-size microfibrils than the Iβ fraction (Yamamoto et al., 1996). Formation of specific NC-CMC composites characterized by an ultrastructure with a lower crystallinity index and thinner microfibrils than normal NC might be the reason for a considerable weakening of their mechanical properties. Data presented in Table 3 clearly show that both the tensile strength and the Young's modulus display the highest values for non-modified bacterial cellulose. Increasing concentrations of CMC in the culture medium causes a gradual decrease in mechanical strength of NC-CMC composite.

TABLE 2

Cellulose $I_\alpha$ and $I_\beta$ content [%] and crystallinity index of nanocellulose from different culture conditions determined by FT-IR measurements.

| CELLULOSE SAMPLE | $I_\alpha$ | $I_\beta$ | IR crystallinity index (abs. at 1427/895 cm$^{-1}$) |
|---|---|---|---|
| *stationary | 76 | 24 | 2.9 |
| *agitated | 71 | 29 | 2.3 |
| agitated with CMC (1.5%) | 54 | 46 | 1.4 |

*data based on the previous paper (Czaja et al, 2004).

In our studies the action of two independent factors: environmental stress occurring while agitation and presence of CMC in the medium result in a significant structural alteration of nanocellulose. Both of these factors disturb the process of nascent cellulose fibril formation based on the following different mechanism of action: possible reduction of intermicrofibrillar hydrogen bonding during agitation and adhesion of CMC on the surface of cellulose microfibrils causing continuous prevention of their further aggregation. As a result, the synthesis of smaller sized cellulose microfibrils has been observed during the action of both factors. Interesting structural characteristics and properties of such a cellulose composite, especially its well-developed surface (consisting of well separated microfibrils) could have important properties, particularly suitable for the pulp industry (especially in the process of paper finishing) or for various processes of bioremediation (heavy metals could easily adhere to the well-developed cellulose surface) as well as for medicine to be used as a modified wound dressing material.

TABLE 3

Mechanical properties of nanocellulose synthesized in the medium containing different % of CMC.

| % of CMC in the medium | Tensile strength [MPa] | Young's modulus [GPa] | Sample thickness [mm] |
|---|---|---|---|
| 0 (control) | 245 | 7.7 | 0.01 |
| 0.1 | 142 | 3.8 | 0.01 |
| 0.3 | 111 | 4.5 | 0.01 |
| 0.7 | 248 | 6.7 | 0.02 |
| 1.0 | 290 | 2.5 | 0.02 |

EXAMPLE 3

The Comparative Studies on 2 Types of Microbial Cellulose Wound Dressings: (1) Xcell® and (2) Nanocellulose.

Macroscopic observations. A microbial cellulose wound dressings have a size of 8.75×8.75 cm and a similar thickness of 1 mm was compared to the nanocellulose wound dressing of the present invention. It was found that the nanocellulose of the present invention has a smoother surface and has a clean white color in comparison to the brownish appearance of Xcell® (data not shown). It was found that the surface of Xcell® seems to be damaged by strong physical processing and that the the texture of Xcell® is softer and more gelatinous than firm texture of Nanocellulose.

Physical properties related to wound healing process. Several different parameters were evaluated to compare the existing microbial cellulose with the nanocellulose of the present invention, namely, rate of evaporation, water vapor transmission rate, absorption rate and water holding capacity.

Rate of evaporation: The microbial cellulose and the nanocellulose wound dressings were kept at 37° C. After regular intervals of time, the loss of weight was noted.

Water vapor transmission rate: The moisture permeability of both the microbial cellulose and the nanocellulose membranes was determined by measuring water vapor transmission rate (WVTR) across the material as suggested by ASTM standards. WVTR=slope×24×1/A [g/m$^2$/day], where A is the test area of the sample in m$^2$.

Absorption rate: The microbial cellulose and the nanocellulose membranes were submerged into a beakers filled with distilled water. At regular intervals of time, the weight of the membranes was noted after removing from water and gently blotting the membranes with a filter paper.

Water holding capacity is described here as ratio of the weight of a wet cellulose membrane to weight of dry cellulose membrane. The calculations were as follows:

$WHC_{Nanocellulose}$ (water holding capacity) of Nanocellulose (wound dressing, not original cellulose membrane)=75 g of water/g cellulose.

$WHC_{Xcell}$ (water holding capacity) of Xcell=127 g of water/g cellulose.

Figure 7:
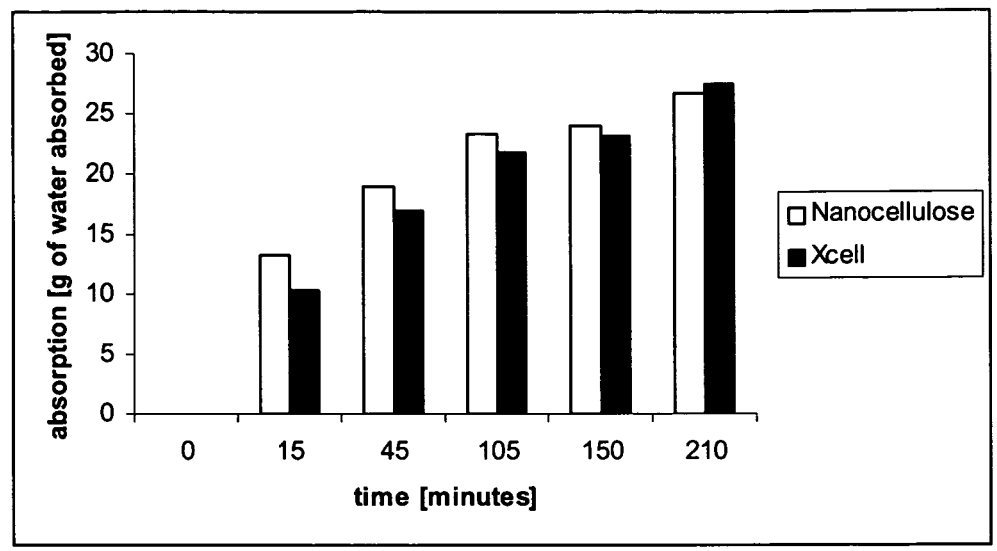
FIG. 7 is a graph that compares the absorption of water by nanocellulose and Xcell wound dressings.

FIG. 7 shows that that microbial cellulose and the nanocellulose wound dressings of the present invention absorb water in similar rate. Xcell® displays a higher WHC, mostly because of a thinner and more relaxed (3-D oriented) structure. The calculations were as follows:

Water vapor transmission rate $WVTR_{Nanocellulose}$=280.86 g/m2/h

Water vapor transmission rate $WVTR_{Xcell}$= 276.9 g/m2/h

Figure 8:
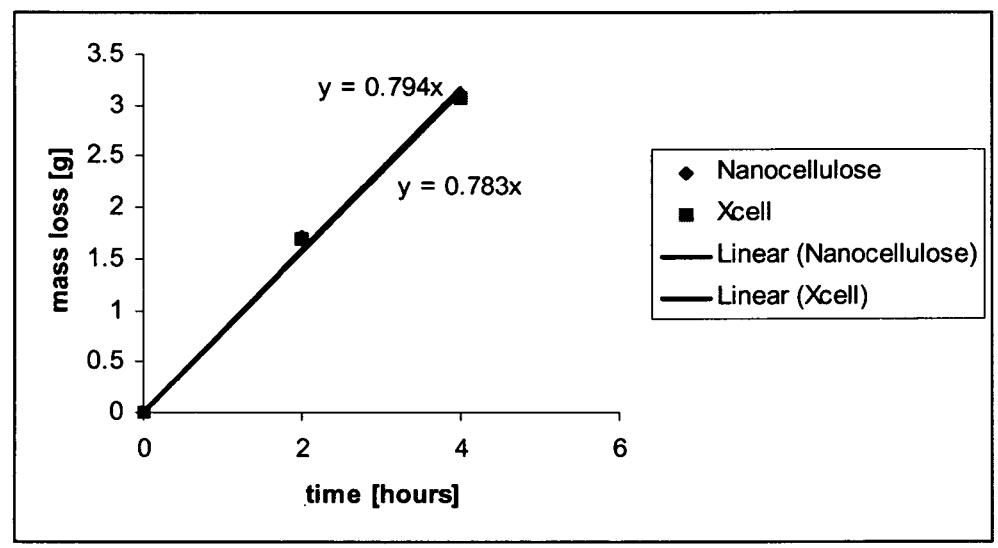
FIG. 8 is a graph that compates the water vapor transmission loss from both cellulose wound dressings.
Figure 9:
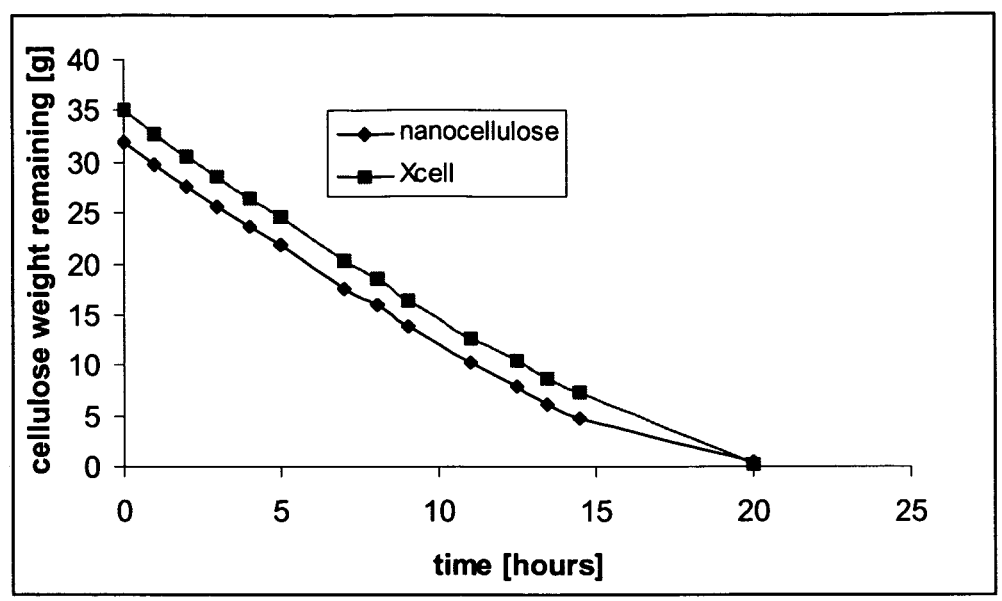
FIG. 9 is a graph that compares the rate of evaporation of water from wound dressing.
Figure 10:
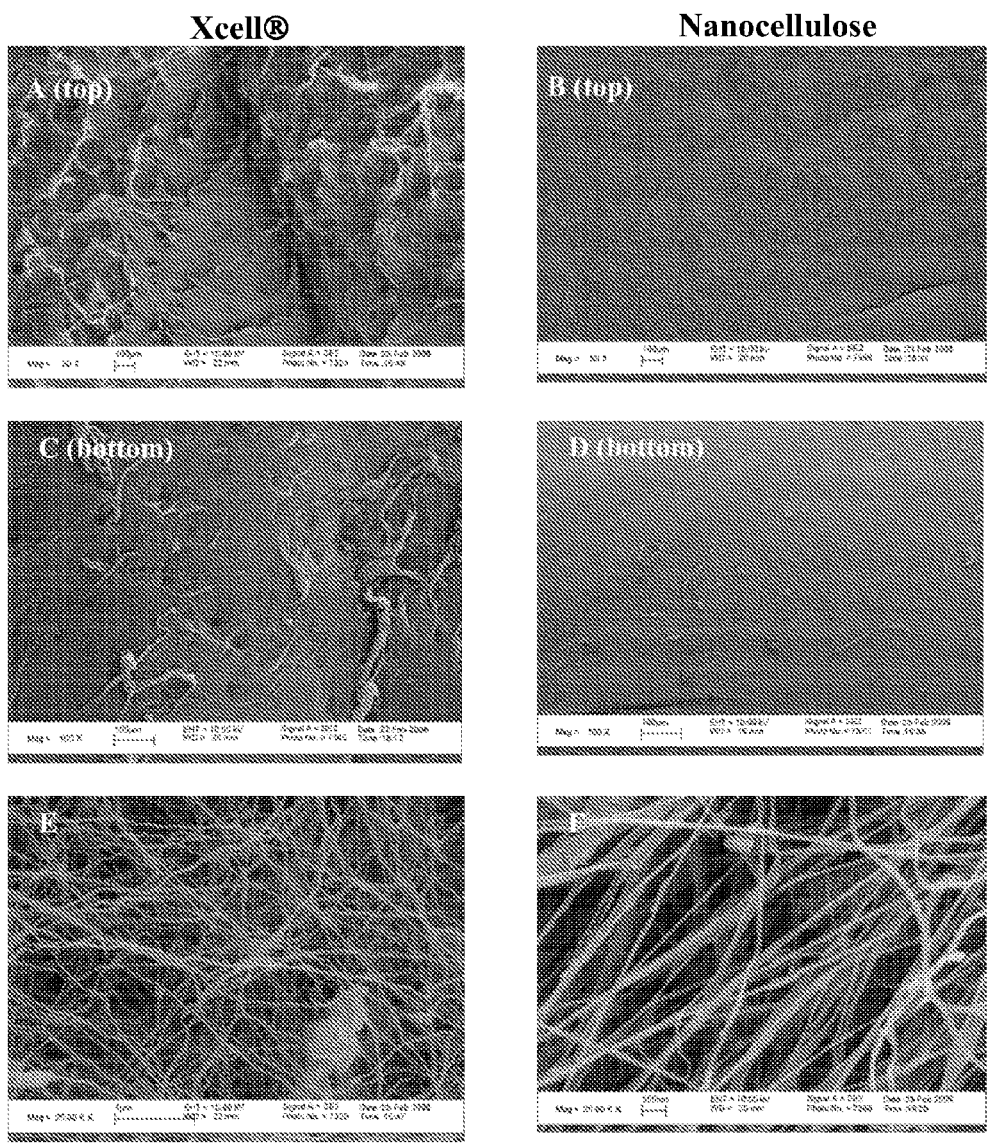
FIG. 10 is a Scanning Electron Microscopy (SEM) comparison of a regular cellulose structure and the nanocellulose of the present invention.
Figure 10:
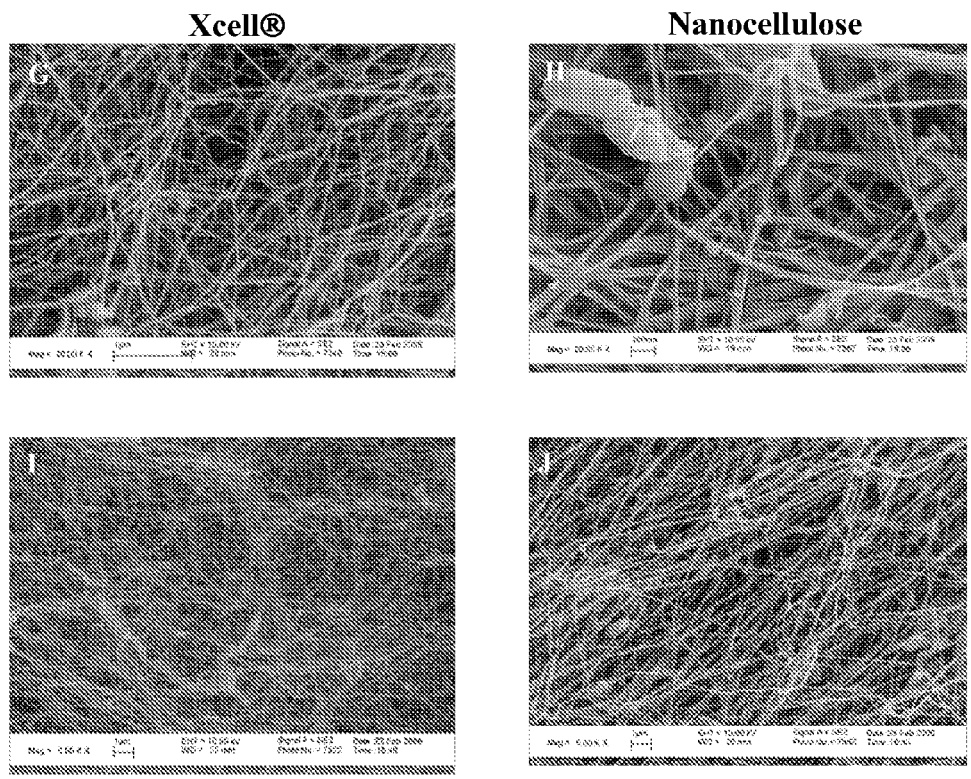
Figure 11:
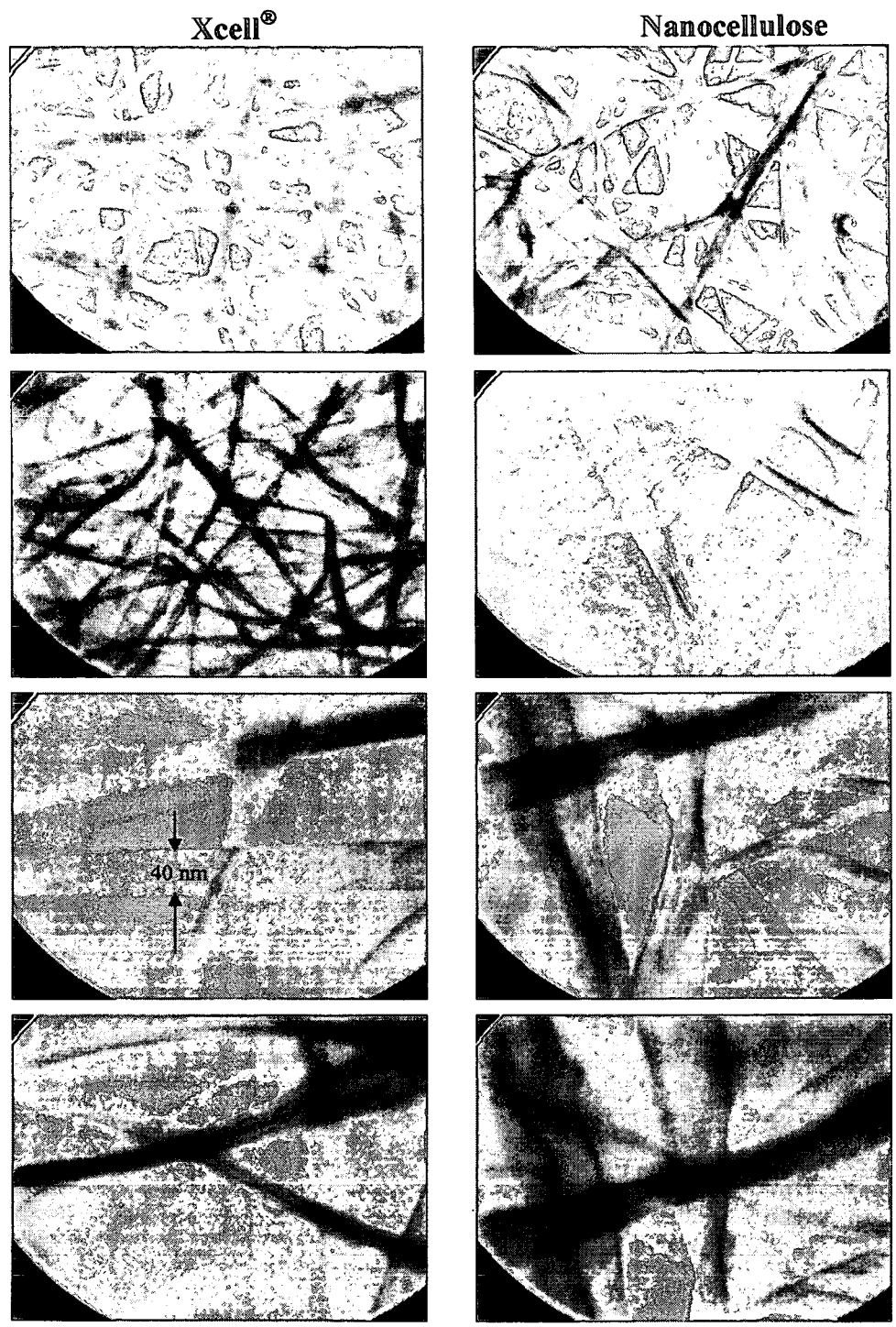
FIG. 11 is a Transmission Electron Microscopy (TEM) comparison of a regular cellulose structure and the nanocellulose of the present invention.

FIG. 8 shows that microbial cellulose and the nanocellulose wound dressings of the present invention are characterized by similar value water vapor transmission rate. The calculations were as follows:

Dry mass of Nanocellulose=0.44 g

Dry mass of Xcell®=0.29 g

EXAMPLE 4

Scanning Electron Microscopy (SEM) observations of cellulose structure. Regular microbial cellulose and the nanocellulose wound dressings of the present invention were dehydrated in stepwise concentrations of ethanol (30%, 50%, 90% and absolute). Samples were then critical point dried (Samdri-790, Tousimis Research Corp.) and then coated with gold (30800, Ladd Research Industries, Inc.). A Leo 1530 field emission scanning electron microscope was used for examination of the samples.

In comparison with smooth surface of nanocellulose wound dressing, the top and bottom surface of Xcell® wound dressing is damaged probably due to a physical processing performed during or after cleaning step (FIGS. 10A-D). The observations of the structure of both cellulose samples at the higher magnifications revealed some major differences in the cellulose ribbon thickness (FIGS. 10E-J). It seems like Nanocellulose is composed of wide and flat ribbons, whereas Xcell® has thin and round ribbons. In other words, it is seems like ribbons of Nanocellulose are characterized by larger size that ribbons of Xcell®. Also it seems like cellulose ribbons of Nanocellulose wound dressing are more one-way oriented in comparison with more 3-D oriented ribbons of Xcell®.

EXAMPLE 5

Transmission Electron Microscopy (TEM) observations of cellulose structure. Specimen were negatively stained and then examined with Philips 420 transmission electron microscope (TEM).

It was found that the average width of cellulose ribbon of Xcell® is around 72 nm, whereas the average width of cellulose ribbon of the nanocellulose of the present invention is about 131 nm. Therefore the average width of a nanocellulose ribbon is almost twice that of an Xcell® ribbon.

EXAMPLE 6

Mechanical testing of cellulose samples. Both cellulose samples were cut into 90×9 mm strips and subjected to mechanical testing using the INSTRON machine.

Figure 12:
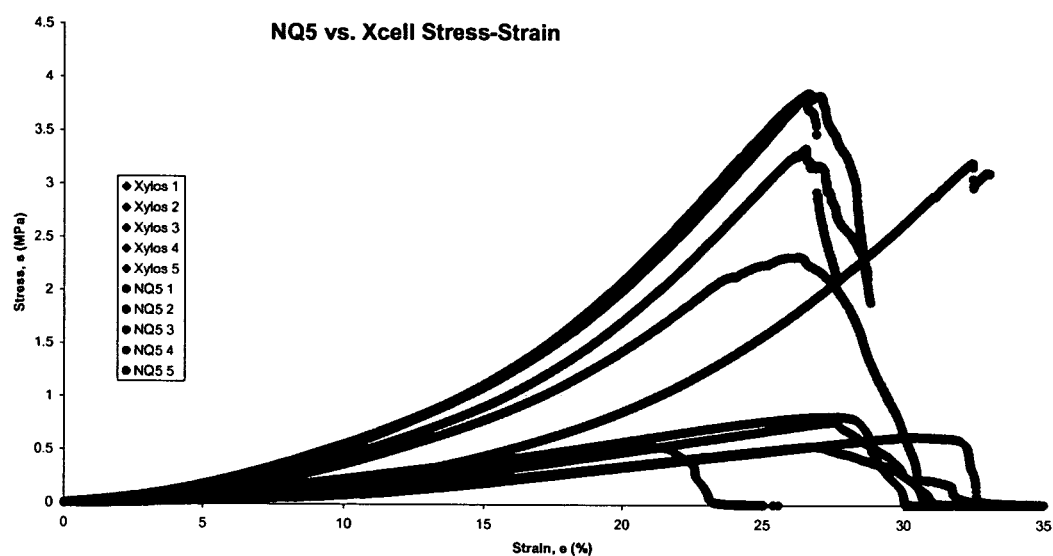
FIG. 12 is a graph that shows the comparison of nanocellulose versus Xcell® wound dressing stress-strain.

The study showed that a Nanocellulose membrane is at least 7 times stronger than an Xcell® membrane (Table 4 and FIG. 12). This result correlates with previous microscopic observations which showed that Nanocellulose ribbons are thicker and wider than ribbons of Xcell®.

TABLE 4

Mechanical properties of Nanocellulose and Xcell ® wound dressings.

| Source of microbial cellulose | Average Young's Modulus [MPa] | Young's Modulus Standard deviation |
|---|---|---|
| Nanocellulose (NQ5) | 25.61 | 4.46 |
| Xcell ® wound dressing | 3.47 | 0.55 |

FIG. 12 is a graph that shows the comparison of nanocellulose versus Xcell® wound dressing stress-strain.

Figure 13:
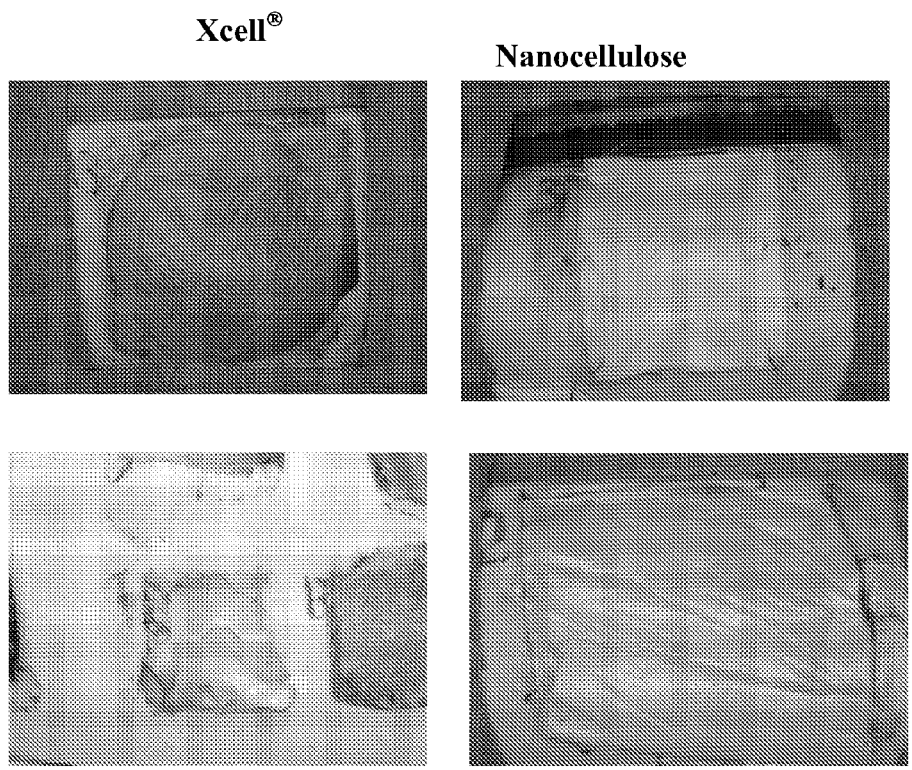
FIG. 13 compares the nanocellulose versus Xcell® wound dressing in a wound model system.

Clinical application of Nanocellulose and Xcell® on partial thickness wounds on pig model. FIG. 13 shows a side by side comparative studies on animal model were performed using the nanocellulose wound dressing of the present invention and Xcell® wound dressing in the treatment of partial-thickness wounds As Xcell® wound dressing is released from the wound it falls apart and the remaining pieces are difficult to remove as they are stacked to the wound surface. The Nanocellulose of the present invention could be removed easily from the wound site and does not stick to underlying surface

EXAMPLE 7

Figure 14:
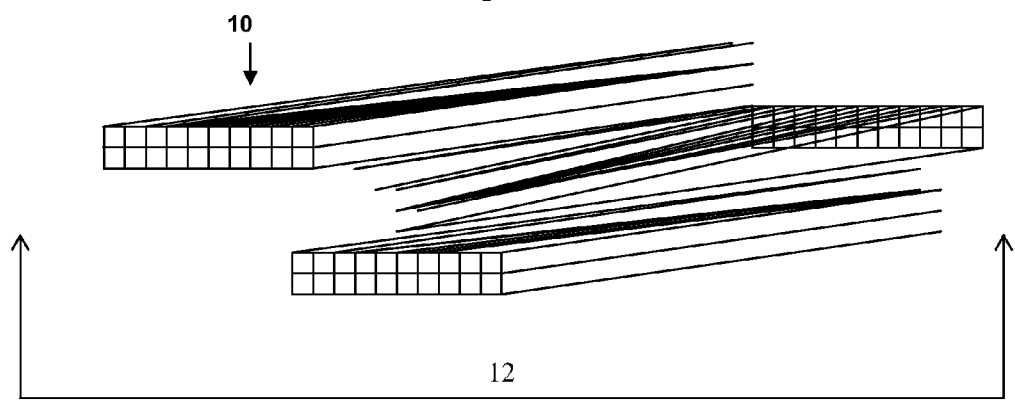
FIG. 14 is a rendering of the ribbon structure of the nanocellulose of the present invention that shows multiple bundles of the regular microbial cellulose that are anti-parallel and give the nanocellulose of the present invention its unique structure.

Multiribbon architecture of naocellulose. The nanocellulose wound dressing of the present invention has a unique cellulose structure, which is distinct and different from any other cellulose wound dressing. As shown in FIG. 14, the unique structure of nanocellulose, which is characterized by its superion physical and mechanical properties for wound healing applications, results from the way the cellulose is deposited from the cells as they move within the liquid environment. This particular structure of cellulose can be generated only by *Acetobacter* organisms which are capable of reversing their direction of movement, depositing a new cellulose ribbon on top of existing ribbon, by which is oriented in the opposite direction of the first. This behavior results in the formation of a bundle of ribbons which are stabilized by hydrogen bonding. As a result of this phenomenon, the mechanical stability and strength are highly improved in comparison with cellulose formed by non-reversing *Acetobacter* strains. These attributes result in a superior cellulose-based wound dressing material that is easier to handle and more effective than other cellulose wound dressings in the treatment of damaged or diseased skin. FIG. 14 shows a drawing that compares the single bundle 10 of cellulose of regular microbial cellulose and a bundle of three (3) cellulose ribbons that form the nanocellulose 14, which are oriented in antiparallel fashion, as a result of the *Acetobacter* cell's reversal of movement.

Conclusions. It was found that the average width of a nanocellulose ribbon is almost twice that of an Xcell® ribbon. The cellulose ribbons of nanocellulose wound dressing are more one-way oriented in comparison with more 3-D oriented ribbons of Xcell®. The nanocellulose wound dressing contains more cellulose than Xcell® (0.44 g and 0.29 g, respectively). The nanocellulose membrane is at least 7 times stronger than an Xcell® membrane. This result correlates well with microscopic observations which showed that nanocellulose ribbons are thicker and wider than ribbons of Xcell®. Microbial cellulose and the nanocellulose wound dressings of the present invention are characterized by similar value of (a) absorption, (b) water vapor transmission rate, and (c) rate of evaporation. Finally, as Xcell® wound dressing is released from the wound it falls apart and the remaining pieces are difficult to remove as they are stacked to the wound surface. In comparison, the nanocellulose can be easily removed from the wound site and does not stick to underlying surface.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the-claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein Without departing from the concept, spirit and scope of the invention. All such similar substitutes and modifications apparent to those skilled in the art are deemed to be within the spirit, scope and concept of the invention as defined by the appended claims.

1. Bielecki S, Krystynowicz A, Turkiewicz M, Kalinowska H. Bacterial cellulose. In: Steinbuchel A, editor. *Biopolymers:* Vol. 5. Polysaccharides I. Wiley-VCH Verlag GmbH, Munster, Gremany, 2002. p. 37-90.
2. Nishi Y, Uryu M, Yamanaka S, Watanabe K, Kitamura N, Iguchi M, Mitsuhashi S. The structure and mechanical properties of sheets prepared from bacterial cellulose. Part 2: improvement of the mechanical properties of sheets and their applicability to diaphragms of electroacoustic transducers. J Mater Sci 1990; 25: 2997-3001.
3. Shah J. and Brown R M, Jr. Towards electronic displays made from microbial cellulose. Appl Microbiol Biotechnol 2005; 66(4): 352-355.
4. Evans B, O'Neill H, Malyvanh V, Lee I, Woodward J. Palladium-bacterial cellulose membranes for fuel cells. Biosens Bioelectron 2003; 18: 917-923.
5. Fontana J D, de Sousa A M, Fontana C K, Torriani I L, Moreschi J C, Gallotti B J, de Sousa S J, Narcisco G P, Bichara J A, Farah L F. *Acetobacter* cellulose pellicle as a temporary skin substitute. Applied biochemistry and biotechnology 1990; 4/25: 253-264.
6. Alvarez O M, Patel M, Booker J, Markowitz L. Effectiveness of a biocellulose wound dressing for the treatment of chronic venous leg ulcers: results of a single center randomized study involving 24 patients. Wounds 2004; 16 (7): 224-233.
7. Czaja W, Kawecki M, Krystynowicz A, Wysota K, Sakiel S, Wroblewski P, Glik J, Bielecki S. Application of bacterial cellulose in treatment of second and third degree burns. The 227th ACS National Meeting, Anaheim, Calif., USA, Mar. 28-Apr. 1, 2004.
8. Brown R M, Jr., Willison J H M, Richardson C L. Cellulose biosynthesis in *Acetobacter xylinum:* 1. Visualization of the site of synthesis and direct measurement of the in vivo process. Proc Nat Acad Sci USA 1976; 73(12): 4565-4569.
9. Ross P, Mayer R, Benziman M. Cellulose biosynthesis and function in bacteria. Microbiol Rev 1991; 55(1): 35-58.
10. Czaja W, Romanovicz D, Brown R M, Jr. Structural investigations of microbial cellulose produced in stationary and agitated culture. Cellulose 2004; 11: 403-411.
11. Krystynowicz A, Czaja W, Pomorski L, Kolodziejczyk M, Bielecki S. The evaluation of usefulness of microbial cellulose as wound dressing material. 14$^{th}$ Forum for Applied Biotechnology, Gent, Belgium, Proceedings Part I, Meded Fac Landbouwwet-Rijksuniv Gent, 2000, p. 213-220.
12. Ring D F, Nashed W, Dow T. Microbial polysaccharide articles and methods of production. U.S. Pat. No. 4,655,758, 1987.
13. Ring D F, Nashed W, Dow T. Liquid loaded pad for medical applications. U.S. Pat. No. 4,588,400, 1986.
14. Farah L F. Process of the preparation of cellulose film, cellulose film produced thereby, artificial skin graft and its use. U.S. Pat. No. 4,912,049, 1990.
15. Brown R M, Jr. Microbial cellulose: A new resource for wood, paper, textiles, food and specialty products. Position Paper. 1999; Internet: http://www.botany.utexas.edu/facstaff/facpages/mbrown/position1.htm
16. Jonas R, Farah L H. Production and application of microbial cellulose. Polymer Degradation and Stability 1998; 59: 101-106.
17. U.S. Congress, Office of Technology Assessment, Biopolymers: Making materials nature's way-background paper, OTA-BP-E-102 (Washington, DC: U.S. Government Printing Office, September 1993): p. 59-60.
18. Krystynowicz A, Galas E. Sposób wytwarzania celulozy bakteryjnej. Patent PL No. 171952B 1, 1997 (in Polish).
19. Krystynowicz A, Czaja W, Bielecki S. Sposób otrzymywania celulozy bakteryjnej, sposób immobilizowania bakterii, sposób otrzymywania immobilizowanych biokatalizatorów, zastosowanie celulozy bakteryjnej, sposób modyfikacji blon celulozowych. Patent PL P361067 pending (in Polish).
20. Bungay H R, Serafica G C. Production of microbial cellulose using a rotating disc film bioreactor. U.S. Pat. No. 5,955,326, 1999.
21. Krystynowicz A, Czaja W, Wiktorowska-Jezierska A, Gongalves-Miskiewicz M, Turkiewicz M, Bielecki S. Factors affecting the yield and properties of bacterial cellulose. Journal of Industrial Microbiology & Biotechnology 2002; 29: 189-195.
22. http://www.xyloscorp.com
23. Vandamme E J, De Baets S, Vanbaelen A, Joris K, De Wulf P. Improved production of bacterial cellulose and its application potential. Polymer Degradation and Stability 1998; 59: 93-99.
24. Martin P. Wound healing-aiming for perfect skin regeneration. Science 1997; 276: 75-81.
25. Balasubramani M, Kumar T R, Babu M. Skin substitutes: a review. Burns 2001; 27: 534-544.
26. Jones I, Currie L, Martin R. A guide to biological skin substitutes. British Journal of Plastic Surgery 2002; 55: 185-193.
27. Walker M, Hobot J A, Newman G R, Bowler P G. Scanning electron microscopic examination of bacterial immobilization in a carboxymethyl cellulose (AQUACEL®) and alginate dressings. Biomaterials 2003; 24: 883-890.
28. Demling R H, DeSanti L. Management of partial thickness facial burns (comparison of topical antibiotics and bio-engineered skin substitutes). Burns 1999; 25: 256-261.
29. Innes M E, Umraw N. Fish J S, Gomez M, Cartotto R C. The use of silver coated dressings on donor site wounds: a prospective, controlled matched pair study. Burns 2001; 27: 621-627.
30. Vloemans A F P M, Soesman A M, Kreis R W, Middelkoop E. A newly developed hydrofibre dressing, in the treatment of partial-thickness burns. Burns 2001; 27: 167-173.
31. Quinn K J, Courtney J M, Evans J H, Gaylor J D S, Reid W H. Principles of burn dressings. Biomaterials 1985; 6: 369-377.
32. Winter G D. Formation of the scab and the rate of epithelization of superficial wounds in the skin of the young domestic pig. Nature 1962; 193: 293-294.
33. Mayall R C, Mayall A C, Mayall L C, Rocha H C, Marques L C. Tratamento das ulceras troficas dos membros corn urn novo substitute da pele. Revista Brasileira de Cirurgia 1990; 80(4): 257-283 (abstract in English).
34. Rebello C, Almeida D A, Lima E M, Jr., Domelas M P. Biofill um novo substituto de pele. Rev Bras Cir 1987; 77(6): 407-414.
35. Wouk A F, Diniz J M, Cirio S M, Santos H, Baltazar E L, Acco A. Membrana biologica (Biofill)—estudo comparative corn outros agentes promotores da cicatrizacao da pele em suinos: aspectos clinicos, histopatologicos e morfometricos. Arch Vet Scienc 1998; 3(1): 31-37 (abstract in English).
36. Slezak A, Kucharzewski M, Sieron A, Golda W, Cieslar G. Testing the osmotic-diffusion properties of the membranous dressing Bioprocess®. Polim Med 1998; 28(3-4): 3-10.
37. Kucharzewski M, Slezak A, Franek A. Topical treatment of non-healing venous ulcers by cellulose membrane. Phlebologie 2003; 32: 147-51.
38. Aung B J. Diabetes watch: Does a new cellulose dressing have a potential in chronic wounds? Podiatry Today 2004; 17(3): 20-26.
39. Latarjet J. A simple guide to burn treatment. Burns 1995; 21: 221-225.
40. Gallin W J, Hepperle B. Burn healing in organ cultures of embryonic chicken skin: a model system. Burns 1998; 24: 613-620.
41. Kawecki M, Krystynowicz A, Wysota K, Czaja W, Sakiel S, Wróblewski P, Glik J Bielecki S. Bacterial cellulose-biosynthesis, properties and applications. International Review Conference Biotechnology, Vienna, Austria, Nov. 14-18, 2004.
42. Watanabe K, Tabuchi M, Morinaga Y, Yoshinaga F. Structural features and properties of bacterial cellulose produced in agitated culture. Cellulose 1998; 5: 187-200.

The invention claimed is:
1. A method of treating a skin wound, comprising the steps of:
making a dry sterile dressing comprising an isolated sheet of multi-ribbon nematic ordered nanocellulose that is substantially non-immunogenic and having a stress-strain strength of 1.0 MPa or greater; and permanently implanting to the wound the dry sterile dressing comprising a substantially non-immunogenic, multi-ribbon sheet of nematic ordered nanocellulose.

2. The method of claim 1, wherein the skin wound comprises a third degree burn.

3. The method of claim 1, further comprising applying an active substance selected from the group consisting of hyaluronan, β-1,3 glucan, carboxymethylcellulose, chitosan, peptides, growth factors, hormones and combinations and mixtures thereof.

4. The method of claim 1, wherein the skin wound comprises a burn.

5. A method of treating a first, second or third degree burn, comprising the steps of:
    making a multi-ribbon nematic ordered nanocellulose dry sterile dressing that is substantially non-immunogenic and is grown under conditions that form a sheet of multi-ribbon nematic ordered cellulose and having a stress-strain strength of 1.0 MPa or greater;
    permanently implanting to a generally skin-less wound the dry sterile dressing comprising a non-immunogenic, multi-ribbon nematic ordered nanocellulose sheet; and
    at least one active substance disposed in, on or about the multi-ribbon nematic ordered nanocellulose sheet, wherein the active agent is disposed within the multi-ribbon nematic ordered nanocellulose sheet before, during or after the manufacture of the multi-ribbon nematic ordered nanocellulose sheet.

6. A method of wound healing comprising the steps of:
    making a substrate that is a dry sterile nanosheet of multi-ribbon nematic ordered nanocellulose that is substantially non-immunogenic and has a stress-strain strength of 1.0 MPa or greater, and is adapted for topical administration; and
    permanently implanting the substrate into a wound wherein the substrate is a nematic ordered nanocellulose, wherein the implanted substrate becomes at least partially integrated into the wound site.

7. The method of claim 6, wherein the substrate becomes permanently integrated into the wound site.

8. The method of claim 6, wherein the substrate is made by one or more prokaryotic organisms that generates cellulose.

9. The method of claim 6, wherein the substrate is made by one or more prokaryotic organisms capable of generating cellulose.

10. The method of claim 6, wherein the substrate is made by one or more prokaryotic organisms selected from *Salmonella, Agrobacterium, Rhizobium, Nostoc, Scytonema* or *Anabaena*.

11. The method of claim 6, wherein the substrate is made by an *Acetobacter* sp., *Acetobacter* multiribbon strain NQ 5 and combinations thereof.

12. The method of claim 6, wherein the substrate is adapted for facial masks, donor sites, chronic wounds, hemostasis, gunshot wounds, knife cuts, bruises, contusions, lacerations and head injuries.

13. A method of treating an open cutaneous wound with a dry substrate comprising implanting an isolated prokaryotic sheet of a dry nematic ordered nanocellulose substrate having a stress-strain strength of 1.0 MPa or greater to a wound bed, wherein at least part of the substrate becomes permanently implanted and the substrate is non-immunogenic.

14. The method of claim 13, wherein the substrate becomes permanently integrated into the wound site.

15. The method of claim 13, wherein the substrate is made by one or more prokaryotic organisms selected from *Salmonella, Agrobacterium, Rhizobium, Nostoc, Scytonema* or *Anabaena*.

16. The method of claim 13, wherein the substrate is made by an *Acetobacter* sp., *Acetobacter* multiribbon strain NQ 5 and combinations thereof.

17. The method of claim 13, wherein the substrate is adapted for facial masks, donor sites, chronic wounds, hemostasis, gunshot wounds, knife cuts, bruises, contusions, lacerations and head injuries.

* * * * *